US007001363B2

(12) United States Patent
Ferguson et al.

(10) Patent No.: US 7,001,363 B2
(45) Date of Patent: Feb. 21, 2006

(54) SAFETY SHIELD FOR MEDICAL NEEDLES

(75) Inventors: F. Mark Ferguson, 1595 E. Treeview Dr., Salt Lake City, UT (US) 84124; Daniel K. Smith, 1473 W. 1540 South, Woods Cross, UT (US) 84087

(73) Assignees: F. Mark Ferguson, Salt Lake City, UT (US); Daniel K. Smith, Woods Cross, UT (US)

( * ) Notice: Subject to any disclaimer, the term of this patent is extended or adjusted under 35 U.S.C. 154(b) by 150 days.

(21) Appl. No.: 10/304,727

(22) Filed: Nov. 26, 2002

(65) Prior Publication Data

US 2003/0191438 A1 Oct. 9, 2003

Related U.S. Application Data

(60) Provisional application No. 60/370,590, filed on Apr. 5, 2002.

(51) Int. Cl.
A61M 5/32 (2006.01)
(52) U.S. Cl. ...................................... 604/198
(58) Field of Classification Search ................ 604/263, 604/264, 268, 272, 187, 192, 198, 110; 128/919
See application file for complete search history.

(56) References Cited

U.S. PATENT DOCUMENTS

| 1,779,451 A | 10/1930 | Sponsel |
| 2,559,474 A | 7/1951 | Son ........................... 128/215 |
| 2,700,385 A | 1/1955 | Ortiz .......................... 128/215 |
| 2,836,942 A | 6/1958 | Miskel .......................... 53/25 |
| 2,854,976 A | 10/1958 | Heydrich ................... 128/221 |
| 2,953,243 A | 9/1960 | Roehr ......................... 206/43 |
| 3,021,942 A | 2/1962 | Hamilton ..................... 206/43 |
| 3,073,307 A | 1/1963 | Stevens ...................... 128/221 |
| 3,074,542 A | 1/1963 | Myerson et al. .............. 206/43 |
| 3,255,873 A | 6/1966 | Speelman .................... 206/56 |
| 3,294,231 A | 12/1966 | Vanderbeck ................. 206/63 |
| 3,323,523 A | 6/1967 | Scislowicz et al. ......... 128/214 |
| 3,329,146 A | 7/1967 | Waldman, Jr. .............. 128/221 |
| 3,333,682 A | 8/1967 | Burke .......................... 206/43 |
| 3,367,488 A | 2/1968 | Hamilton ..................... 206/63 |
| 3,485,239 A | 12/1969 | Vanderbeck ................ 128/218 |
| 3,537,452 A | 11/1970 | Wilks ......................... 128/214 |
| 3,587,575 A | 6/1971 | Lichtenstein ............... 128/215 |
| 3,610,240 A | 10/1971 | Harautuneian ............. 128/214 |
| 3,658,061 A | 4/1972 | Hall .......................... 128/214 |

(Continued)

FOREIGN PATENT DOCUMENTS

EP 0 344 606 A2 12/1989

(Continued)

*Primary Examiner*—Manuel Mendez
(74) *Attorney, Agent, or Firm*—Paul S. Evans

(57) ABSTRACT

A medical needle shield apparatus is provided that includes a shield being extensible from a retracted position to an extended position, wherein the shield includes a first segment mounted to a medical needle device having a needle extending therefrom. The shield further includes a second segment articulating from the first segment and a third segment articulating from the first segment, wherein the second segment includes an engagement surface. The shield further includes a fourth segment articulating from the second segment and the third segment. The engagement surface of the second segment is engageable to urge the shield from the retracted position such that the second segment and the third segment cooperate to extend the shield to the extended position, whereby the fourth segment substantially encloses a distal end of the needle.

33 Claims, 37 Drawing Sheets

U.S. PATENT DOCUMENTS

| | | | |
|---|---|---|---|
| 3,828,775 A | 8/1974 | Armel | 128/218 |
| 3,840,008 A | 10/1974 | Noiles | 128/221 |
| 3,890,971 A | 6/1975 | Leeson et al. | 128/218 |
| 3,904,033 A | 9/1975 | Haerr | 206/349 |
| 3,934,722 A | 1/1976 | Goldberg | 206/365 |
| 3,968,876 A | 7/1976 | Brookfield | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/198 |
| 4,702,738 A | 10/1987 | Spencer | 604/198 |
| 4,723,943 A | 2/1988 | Spencer | 604/198 |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A * | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 128/164 |
| 4,790,828 A | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 128/764 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | 604/198 |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | 604/198 |
| 4,863,435 A | 9/1989 | Sturman et al. | 604/198 |
| 4,863,436 A | 9/1989 | Glick | 604/198 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A * | 1/1990 | Laico et al. | 604/192 |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A | 6/1990 | Haber et al. | 604/192 |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A | 8/1990 | Haber et al. | 604/192 |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 5,000,744 A | 3/1991 | Hoffman et al. | 604/232 |
| 5,015,240 A | 5/1991 | Soproni et al. | 604/192 |
| 5,057,089 A | 10/1991 | Greco | 604/198 |
| 5,059,180 A | 10/1991 | McLees | 604/110 |
| 5,092,851 A | 3/1992 | Ragner | 604/192 |
| 5,108,379 A | 4/1992 | Dolgin et al. | 604/198 |
| RE34,045 E | 8/1992 | McFarland | 604/198 |
| 5,135,509 A | 8/1992 | Olliffee | 604/192 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 604/198 |
| 5,250,031 A | 10/1993 | Kaplan et al. | 604/110 |
| 5,254,099 A | 10/1993 | Kuracina et al. | 604/198 |
| 5,256,152 A | 10/1993 | Marks | 604/198 |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,304,137 A | 4/1994 | Fluke | 604/110 |
| 5,312,369 A | 5/1994 | Arcusin et al. | 604/192 |
| 5,334,158 A | 8/1994 | McLees | 604/110 |
| 5,348,544 A | 9/1994 | Sweeney et al. | 604/192 |
| 5,356,392 A | 10/1994 | Firth et al. | 604/198 |
| 5,403,283 A | 4/1995 | Luther | 604/164 |
| 5,403,286 A | 4/1995 | Lockwood, Jr. | 604/110 |
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |
| 5,423,766 A | 6/1995 | Di Cesare | 604/192 |
| 5,425,720 A | 6/1995 | Rogalsky et al. | 604/198 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,498,243 A | 3/1996 | Vallelunga et al. | 604/197 |
| 5,531,694 A | 7/1996 | Clemens et al. | 604/110 |
| 5,533,980 A | 7/1996 | Sweeney et al. | 604/192 |

| | | | | | | | |
|---|---|---|---|---|---|---|---|
| 5,538,508 A | 7/1996 | Stern | 604/192 | 6,149,629 A | 11/2000 | Wilson et al. | 604/198 |
| 5,542,927 A | 8/1996 | Thorne et al. | 604/110 | 6,171,284 B1 | 1/2001 | Kao et al. | 604/192 |
| 5,549,568 A | 8/1996 | Shields | 604/192 | RE37,110 E | 3/2001 | Hollister | 206/365 |
| 5,549,570 A | 8/1996 | Rogalsky | 604/198 | RE37,252 E | 7/2001 | Hollister | 206/364 |
| 5,549,708 A | 8/1996 | Thorne et al. | 604/110 | 2002/0004650 A1 | 1/2002 | Kuracina et al. | |
| 5,562,629 A | 10/1996 | Haughton et al. | 604/158 | | | | |
| 5,562,631 A | 10/1996 | Bogert | 604/164 | FOREIGN PATENT DOCUMENTS | | | |
| 5,573,510 A | 11/1996 | Isaacson | 604/158 | EP | 0 457 477 B1 | 11/1991 | |
| 5,584,816 A | 12/1996 | Gyure et al. | 604/192 | EP | 0 485 345 B1 | 5/1992 | |
| 5,584,818 A | 12/1996 | Morrison | 604/197 | EP | 0 533 308 A1 | 3/1993 | |
| 5,643,220 A | 7/1997 | Cosme | 604/192 | EP | 0 654 281 B1 | 5/1995 | |
| 5,672,161 A | 9/1997 | Allen et al. | 604/263 | EP | 0 705 613 B1 | 4/1996 | |
| 5,695,474 A | 12/1997 | Daugherty | 604/162 | EP | 0 713 710 A1 | 5/1996 | |
| 5,695,477 A | 12/1997 | Sflkas | 604/241 | EP | 0 815 888 A2 | 1/1998 | |
| 5,700,249 A | 12/1997 | Jenkins | 604/263 | EP | 0 815 890 A2 | 1/1998 | |
| 5,735,827 A | 4/1998 | Adwers et al. | 604/263 | EP | 0 819 441 A1 | 1/1998 | |
| 5,738,665 A | 4/1998 | Caizza et al. | 604/263 | EP | 0 832 659 A2 | 4/1998 | |
| 5,746,718 A | 5/1998 | Steyn | 604/192 | EP | 0 832 660 A2 | 4/1998 | |
| 5,746,726 A | 5/1998 | Sweeney et al. | 604/263 | GB | 1233302 | 5/1971 | |
| 5,755,699 A | 5/1998 | Blecher et al. | 604/198 | GB | 2 283 429 A | 5/1995 | |
| 5,814,018 A | 9/1998 | Elson et al. | 604/110 | JP | 10-76007 | 3/1998 | |
| 5,823,997 A | 10/1998 | Thorne | 604/110 | JP | 10-127765 | 5/1998 | |
| 5,843,041 A | 12/1998 | Hake et al. | 604/198 | WO | WO 92/20390 | 5/1991 | |
| 5,910,130 A | 6/1999 | Caizza et al. | 604/110 | WO | WO 93/02728 | 8/1991 | |
| 5,919,168 A | 7/1999 | Wheeler | 604/198 | WO | WO 94/01152 | 6/1993 | |
| 5,925,020 A | 7/1999 | Nestell | 604/198 | WO | WO 97/31666 | 9/1997 | |
| 5,957,892 A | 9/1999 | Thorne | 604/162 | WO | WO 00/16832 | 3/2000 | |
| 5,980,488 A | 11/1999 | Thorne | 604/110 | | | | |
| 6,015,397 A | 1/2000 | Elson et al. | 604/192 | * cited by examiner | | | |
| 6,036,675 A | 3/2000 | Thorne et al. | 604/232 | | | | |

SAFETY SHIELD FOR MEDICAL NEEDLES

CROSS-REFERENCE TO RELATED APPLICATIONS

This patent application claims priority from U.S. Provisional Patent Application Ser. No. 60/370,590, filed in the U.S. Patent and Trademark Office on Apr. 5, 2002 by Ferguson et al., the entire contents of which being hereby incorporated by reference herein.

BACKGROUND

1. Technical Field

The present disclosure generally relates to safety shields for medical needles, and more particularly, to safety shields that are extensible to shield a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the wound than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield needle infusion and/or fluid collection apparatus to prevent hazardous exposure.

Consequently, there remains a need to provide a more satisfactory solution for needle safety devices by overcoming the disadvantages and drawbacks of the prior art. Therefore, a need remains to provide a more satisfactory solution for needle safety devices by overcoming the disadvantages and drawbacks discussed hereinabove.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a shield being extensible from a retracted position to an extended position, wherein the shield includes a first segment mounted to a medical needle device having a needle extending therefrom. The shield further includes a second segment articulating from the first segment and a third segment articulating from the first segment, wherein the second segment includes an engagement surface. The shield further includes a fourth segment articulating from the second segment and the third segment. The engagement surface of the second segment is engageable to urge the shield from the retracted position such that the second segment and the third segment cooperate to extend the shield to the extended position, whereby the fourth segment substantially encloses a distal end of the needle.

The first segment is cylindrical and fixedly mounted to the distal end of a syringe. The first segment may include at least one latch for lockingly engaging with at least one catch associated with the fourth segment when the shield is in the retracted position. Moreover, the fourth segment includes a nose portion and a lock, wherein the lock engages the needle when the shield is in the extended position and wherein the nose portion defines a cavity for disposal of the needle when the shield is in the extended position.

In an alternate embodiment, a medical needle shield apparatus is provided and includes a shield having a plurality of articulating segments that facilitate extension of the shield from a retracted position to an extended position. The plurality of segments includes a first segment defining a collar, wherein the collar includes an inner surface that defines a cavity and wherein the inner surface includes at least one radially inward projecting collar stop.

Additionally, a mounting ring configured for mounting to a medical needle device is provided, wherein the mounting ring includes an outer surface having at least one radially outward projecting proximal stop and at least one radially projecting distal stop, wherein the collar is configured for relative rotational movement with the mounting ring such that the outer surface of the mounting ring is disposed within the cavity of the collar and wherein the at least one collar stop is disposed adjacent the outer surface of the mounting ring such that the at least one proximal stop prevents distal axial movement, relative to a longitudinal axis of the medical needle device, of the collar and the at least one distal stop prevents proximal axial movement of the collar.

In another embodiment, a medical needle shield apparatus is provided and includes a shield extensible from a retracted position to an extended position, wherein the shield includes a cylindrical collar, a proximal segment articulating from the collar, a manual actuator articulating from the collar and a distal segment articulating from the proximal segment and the manual actuator. The collar defines an inner surface that defines a cavity, wherein the inner surface includes a plurality of radially inward projecting collar stops that are equidistantly spaced about the inner surface. The manual actuator includes an engagement surface that is engageable to urge the shield from the retracted position such that the manual actuator and the proximal segment cooperate to extend the shield to the extended position, whereby the distal segment includes a nose portion that substantially encloses a distal end of a needle extending from a syringe.

Additionally, a mounting ring configured for mounting to the syringe is provided and includes an outer surface that includes a plurality of radially outward projecting proximal stops that are equidistantly spaced about the outer surface and a plurality radially projecting distal stops that are equidistantly spaced about the outer surface, wherein the collar is configured for relative rotational movement with the mounting ring such that the mounting ring is disposed in an interlocking orientation with the collar and whereby the plurality of collar stops are disposed adjacent the outer surface of the mounting ring such that the plurality of proximal stops prevent distal axial movement, relative to a longitudinal axis of the syringe, of the collar and the plurality of distal stops prevent proximal axial movement of the collar.

BRIEF DESCRIPTION OF THE DRAWINGS

The foregoing and other features and advantages of the present disclosure will be more fully understood from the following detailed description of the illustrative embodiments, taken in conjunction with the accompanying drawings in which.

DETAILED DESCRIPTION OF THE EXEMPLARY EMBODIMENTS

Figure 1:
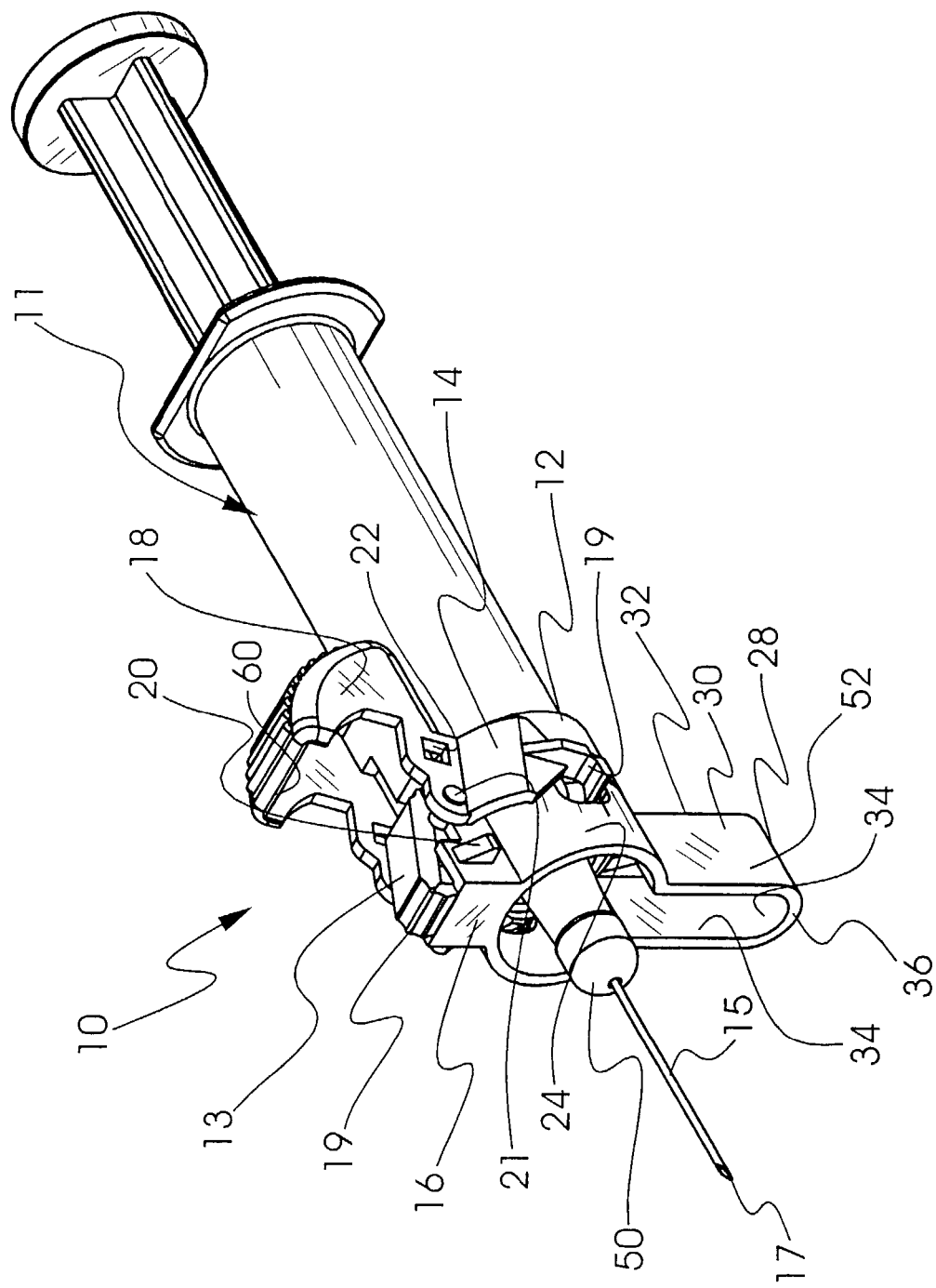
FIG. 1 is a perspective view of a medical needle shield apparatus in a retracted position, in accordance with the principles of the present invention.
Figure 2:
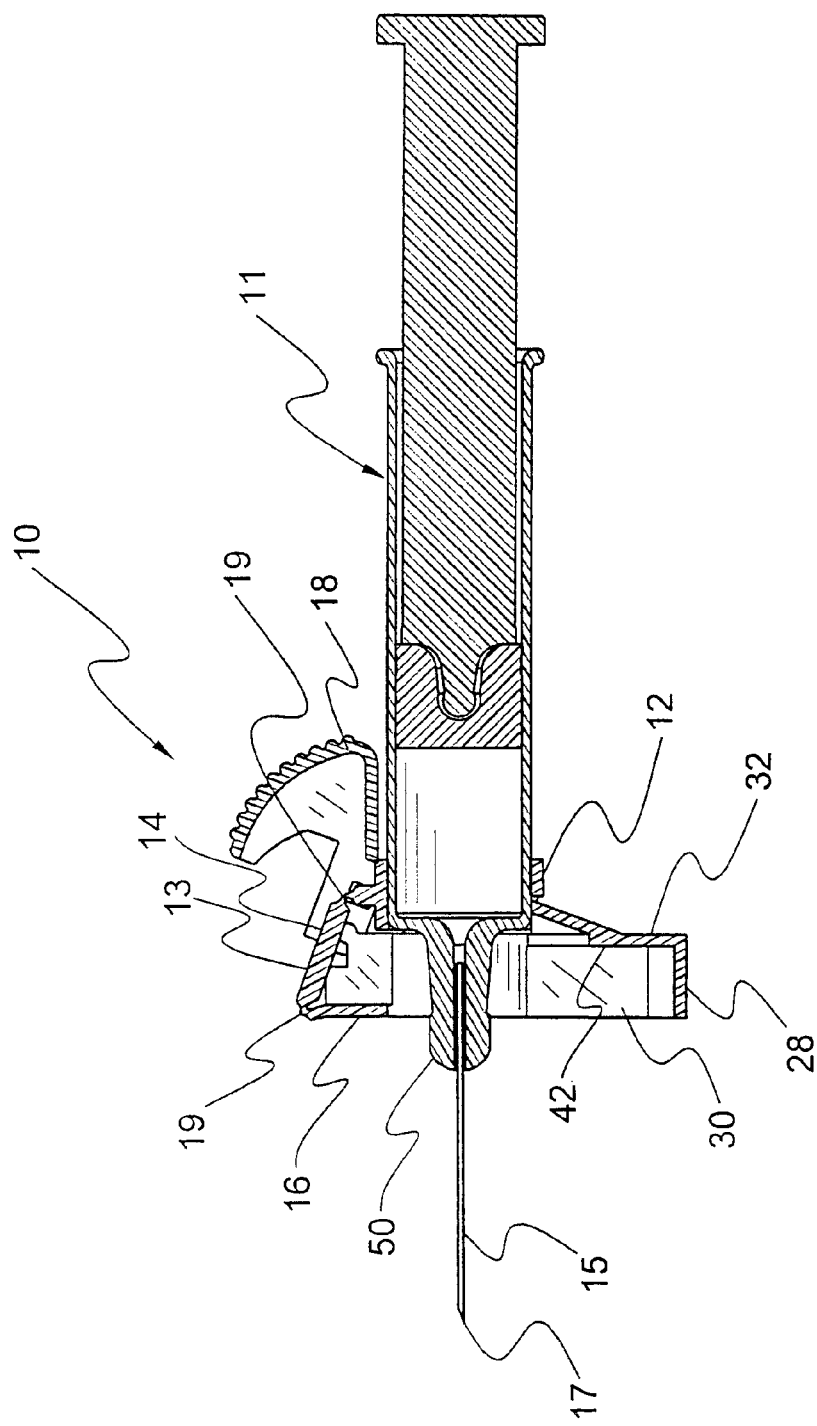
FIG. 2 is a cross-sectional view of the medical needle shield apparatus shown in FIG. 1.
Figure 3:
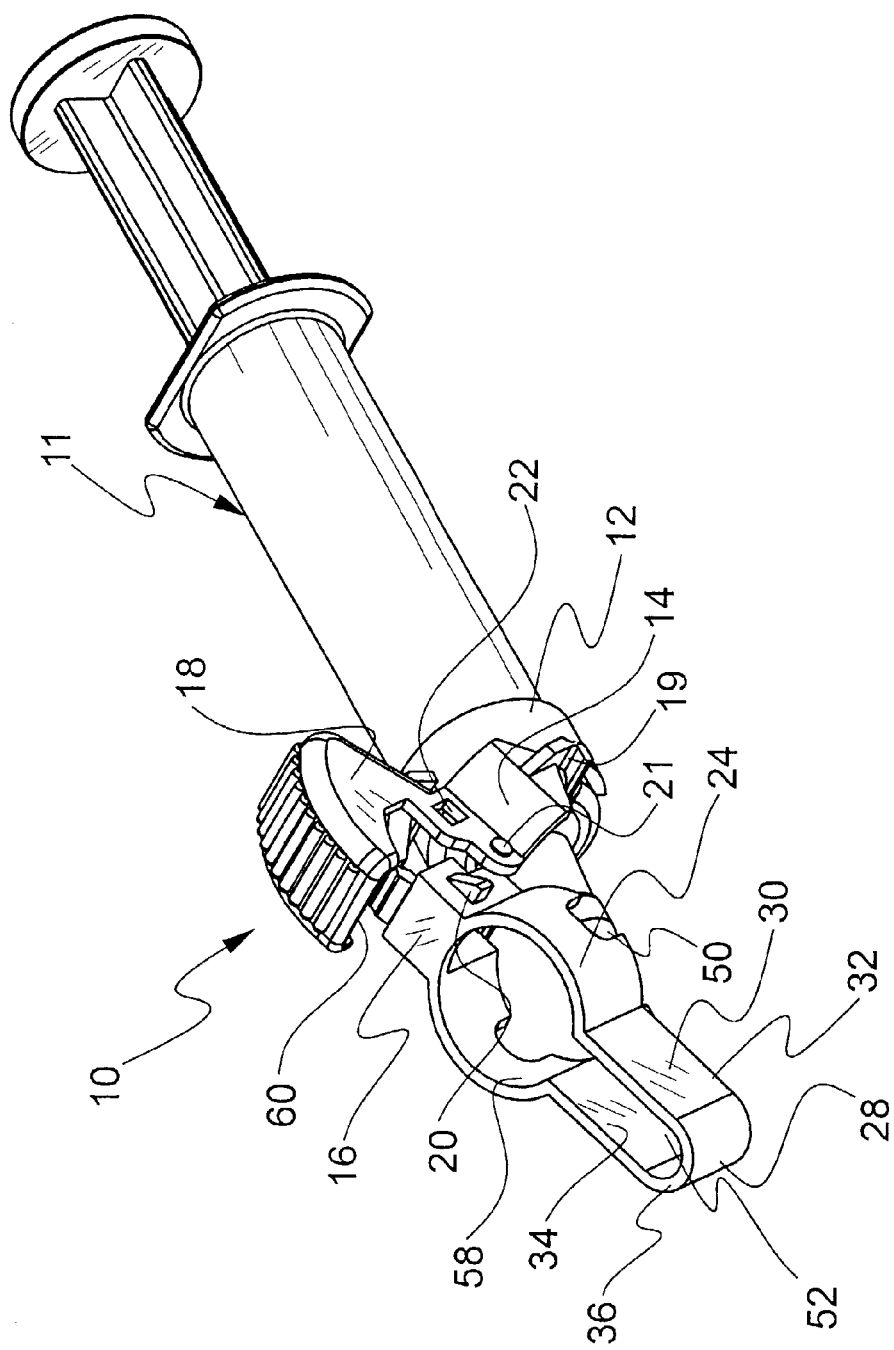
FIG. 3 is a perspective view of the medical needle shield apparatus illustrated in FIG. 1 at mid-extension.
Figure 4:
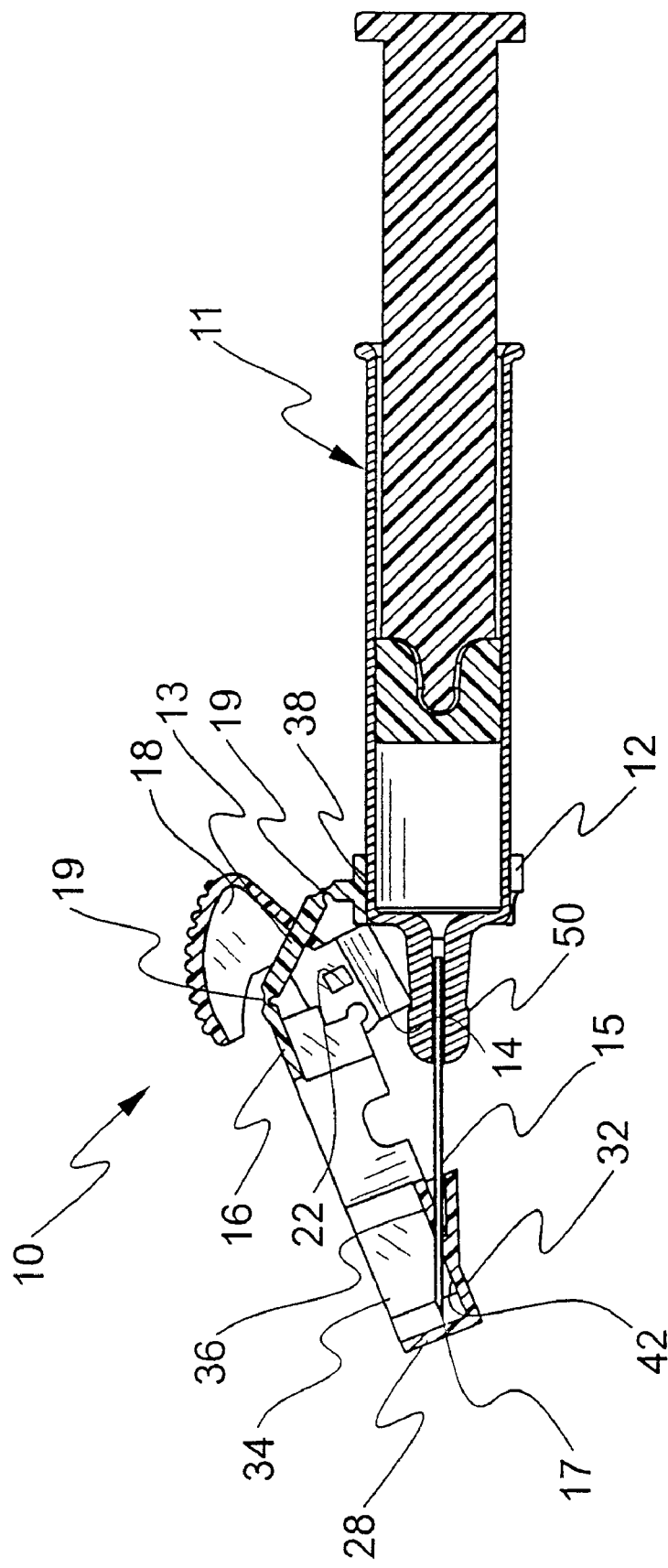
FIG. 4 is a cross-sectional view of the medical needle shield apparatus shown in FIG. 3.
Figure 5:
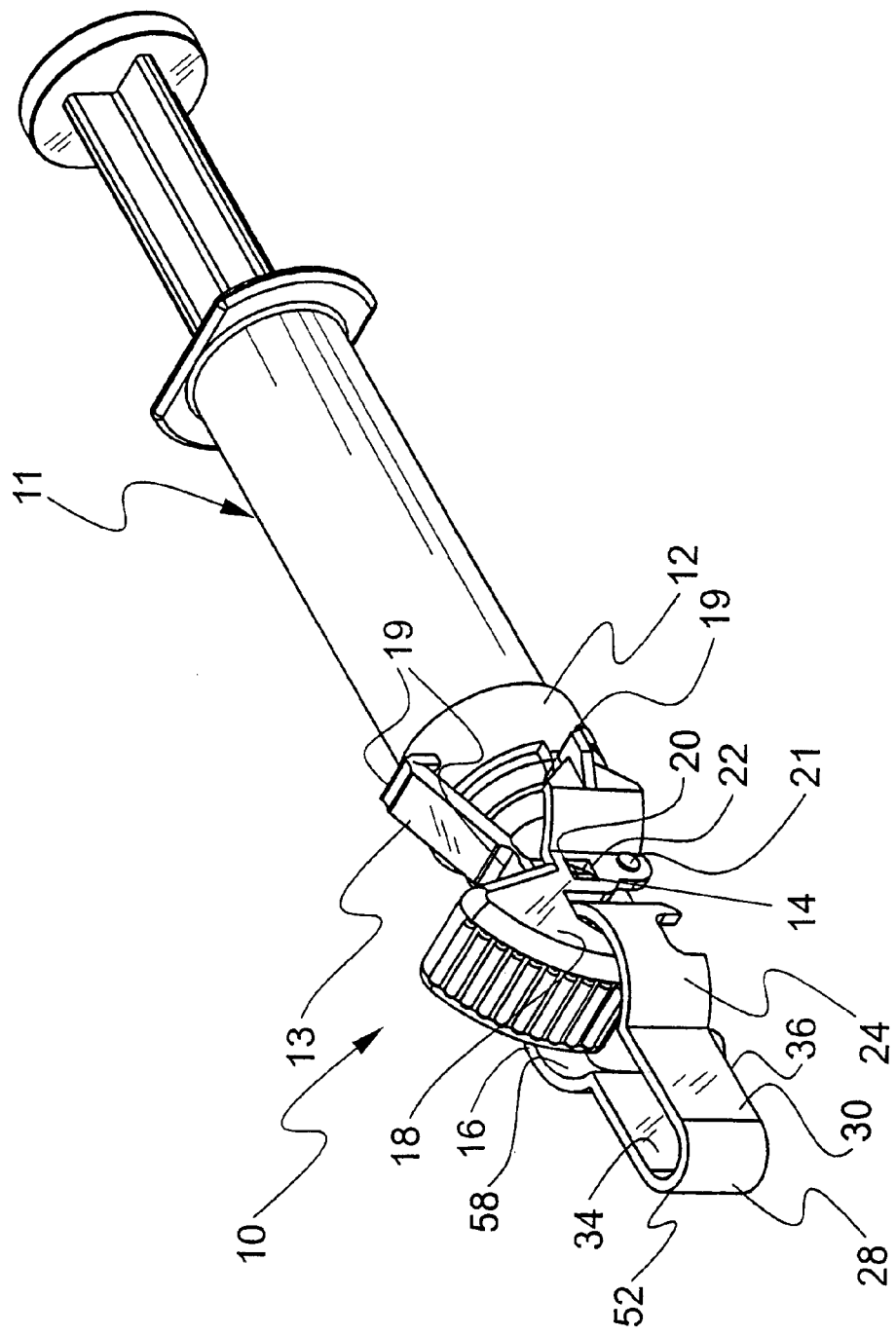
FIG. 5 is a perspective view of the medical needle shield apparatus illustrated in FIG. 1 fully extended.
Figure 6:
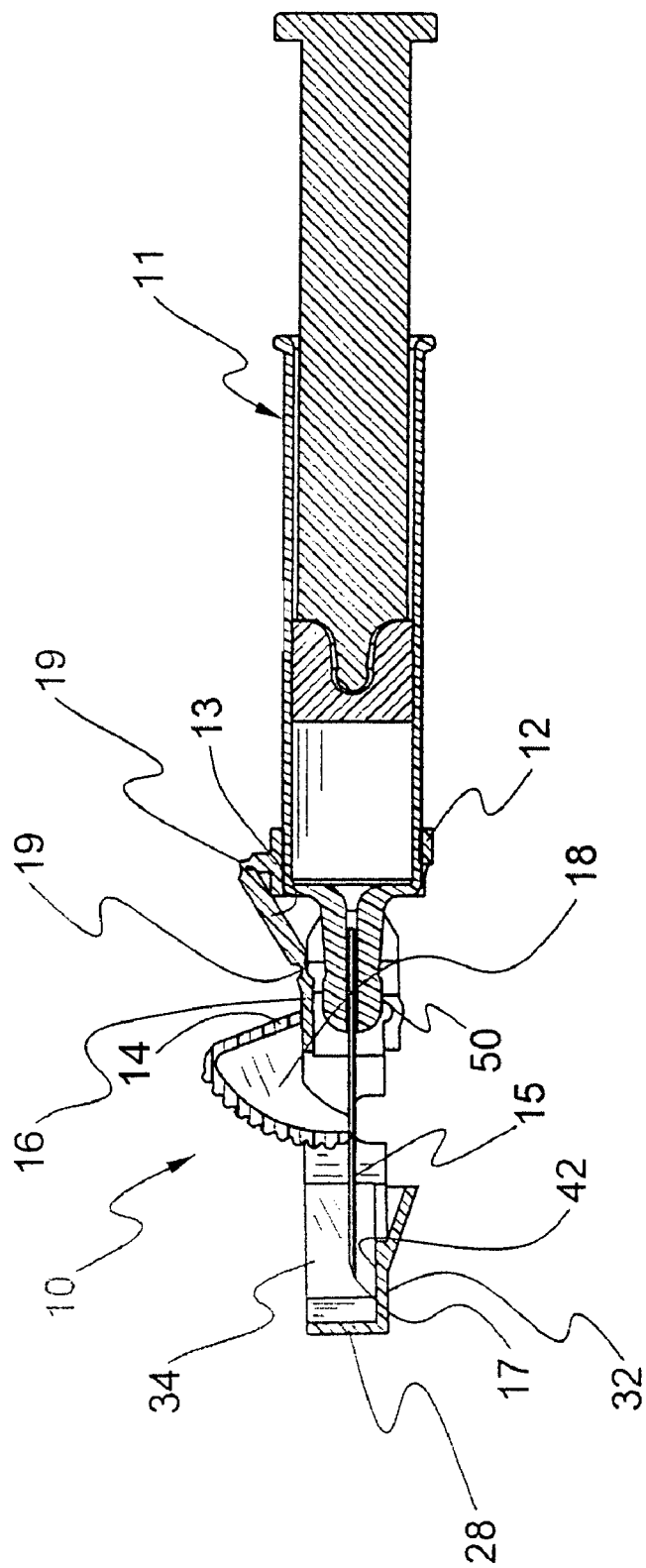
FIG. 6 is a cross-sectional view of the medical needle shield apparatus shown in FIG. 5.

The exemplary embodiments of the medical needle shield apparatus and methods of operation disclosed are discussed in terms of medical needles for infusion of intravenous fluids, medication infusion or fluid collection, and more particularly, in terms of needle shield apparatus employed with a needle cannula that prevent hazardous exposure to the needle cannula, including, for example, inadvertent needle sticks. It is contemplated that the needle cannula may be shielded during use including storage, transport, fluid infusion and/or collection, subsequent thereto, etc. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is contemplated that the medical needle shield apparatus may be utilized with other medical needle applications including phlebotomy devices, catheters, catheter introducers, guide wire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–13, there is illustrated a medical needle shield apparatus including an extensible shield, such as, for example, safety shield 10, constructed in accordance with the principles of the present disclosure. Safety shield 10 is advantageously configured to prevent hazardous exposure to a needle cannula 15 by providing an adequate and reliable medical needle shield apparatus for a needle infusion and/or fluid collection device which shields a needle via one handed operation, as will be discussed below.

Safety shield 10 is attached to a medical needle device, such as, for example, a syringe 11 to facilitate safe infusion of fluids to a subject (not shown) from a sterile cartridge or the like. Safety shield 10 may be attached to syringe 11 via spin welding, adhesive, other welding methods, etc. Alternatively, safety shield 10 may be monolithically, integrally connected, etc. with the distal end of syringe 11. Safety shield 10 is employed with a needle cannula 15 supported by a needle hub 50 of syringe 11. It is contemplated that a syringe employed may be prefilled with a fluid, such as a pharmaceutical medication or may be a prefillable syringe which is subsequently filled with a medication. It is further contemplated that safety shield 10 may be used with other fluid infusion, fluid collection, catheters, introducers, etc., similar to those described above.

Safety shield 10 includes a four-bar linkage, wherein a first segment, such as, for example, a collar 12 is configured as the fixed link with a second segment, such as, for example, proximal linkage 14, a fourth segment, such as, for example, distal linkage 16, and a third segment, such as, for example, input linkage 13 extending therefrom. Distal linkage 16 includes a circumferential wall, such as, for example, a cylinder 24. Cylinder 24 is disposed about needle cannula 15 and configured to facilitate extension of safety shield 10 between a retracted position (FIG. 1) and an extended position (FIG. 5), as will be discussed. Input linkage 13 is configured so that the shield 10 is not required to engage the needle 15 during extension of the shield 10 to the extended position.

Distal linkage 16 defines a planar surface, such as, for example, a base 32, discussed in more detail below, adjacent a distal portion 52 thereof. Base 32 is configured to engage needle cannula 15 for disposing safety shield 10 in the extended position.

Thus, another advantage of the present disclosure is that safety shield 10 is easily extendable via one handed activation, resulting in a higher degree of safety to the clinician and subject. Further, this configuration of safety shield 10 advantageously provides guided extension of the shield to reliably prevent hazardous exposure to needle cannula 15 during manipulation.

Safety shield 10 is desirably contemplated for use in the field of medical fluid infusion and/or collection. More particularly, safety shield apparatus 10 is envisioned to be a disposable needle device employing, among other things, safety features having shielding capabilities to prevent inadvertent sticking or punctures of clinicians and subjects, as well as uniform and dependable movement during a procedure and a locking mechanism for reliable use. The above advantages, among others, realized from the present disclosure are attained through the disclosed safety shield 10, which is extensible to a protective configuration, as discussed hereinbelow. These features of the present disclosure advantageously facilitate a safe infusion and/or collection of fluids and prevent inadvertent needle stick of a clinician and subject.

Safety shield 10 is monolithically formed. It is contemplated, however, that the component parts of safety shield 10 may be integrally assembled. Safety shield 10 can be fabricated from a material suitable for medical applications, such as, for example, polymerics, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate. Alternatively, portions of safety shield 10 can be monolithically formed and assembled therewith.

Proximal linkage 14 is articulated to a collar 12 via a hinged connection. It is contemplated that the hinged connection of proximal linkage 14 to collar 12 may be living hinges, pinned hinges, etc., or alternatively, may be movably connected by other structure, such as, ball joint, etc. This configuration provides movement of proximal linkage 14 relative to collar 12, facilitating extension of safety shield 10. It is envisioned that one or a plurality of hinged connections may be used. Collar 12 is fixedly mounted to an outer surface of a distal end 38 of syringe 11. Collar 12 may also be mounted directly to needle hub 50 or various portions of syringe 11.

Figure 7:
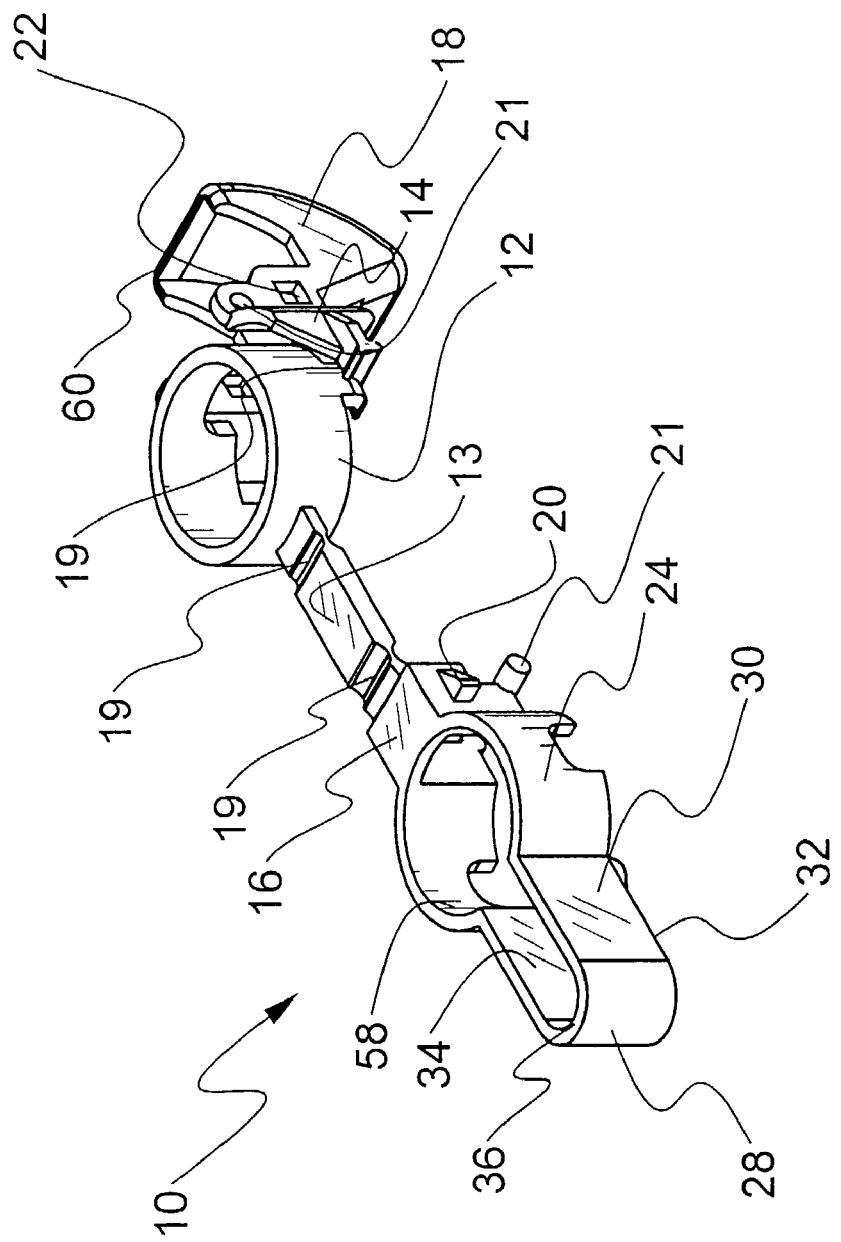
FIG. 7 is a view of the medical needle shield apparatus illustrated in FIG. 1 prior to attachment to a medical needle device.
Figure 8:
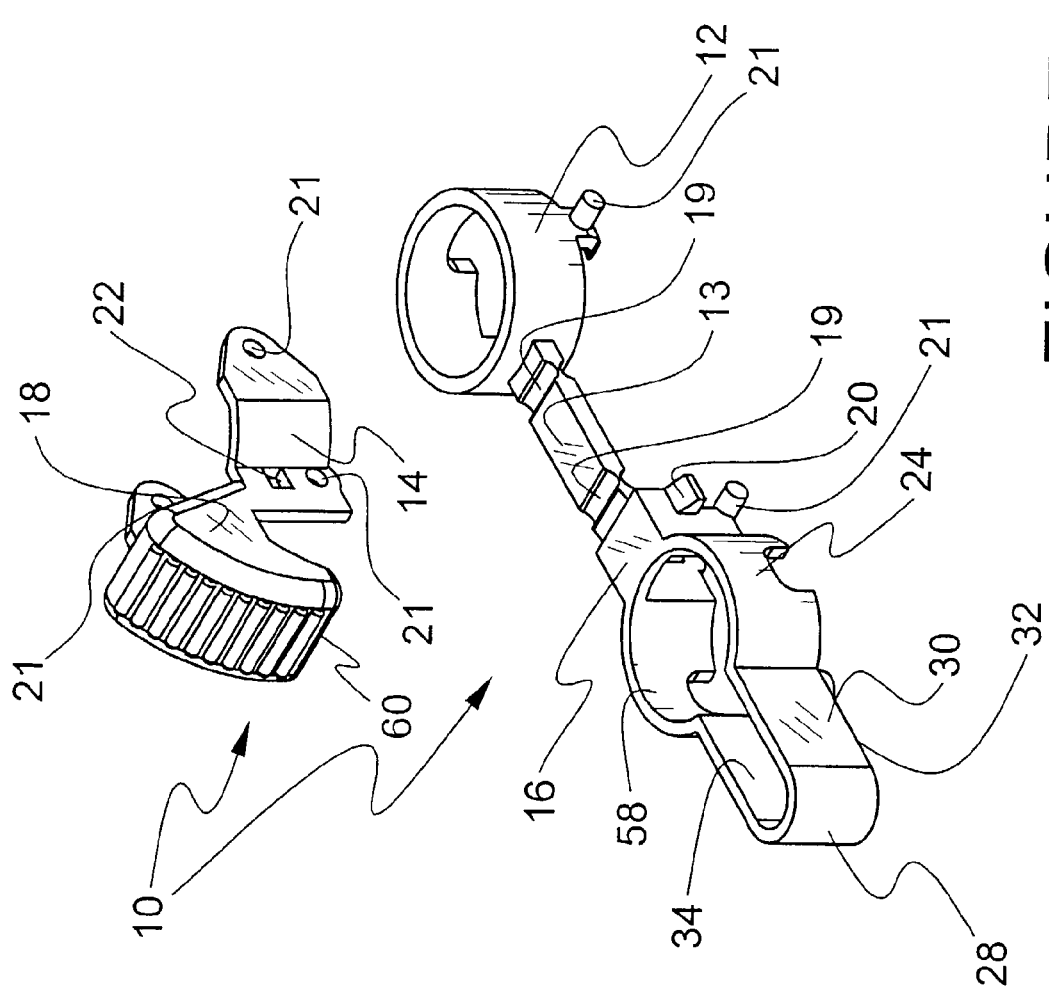
FIG. 8 is a view of the medical needle shield apparatus illustrated in FIG. 1 showing an alternate embodiment of hinges.
Figure 12:
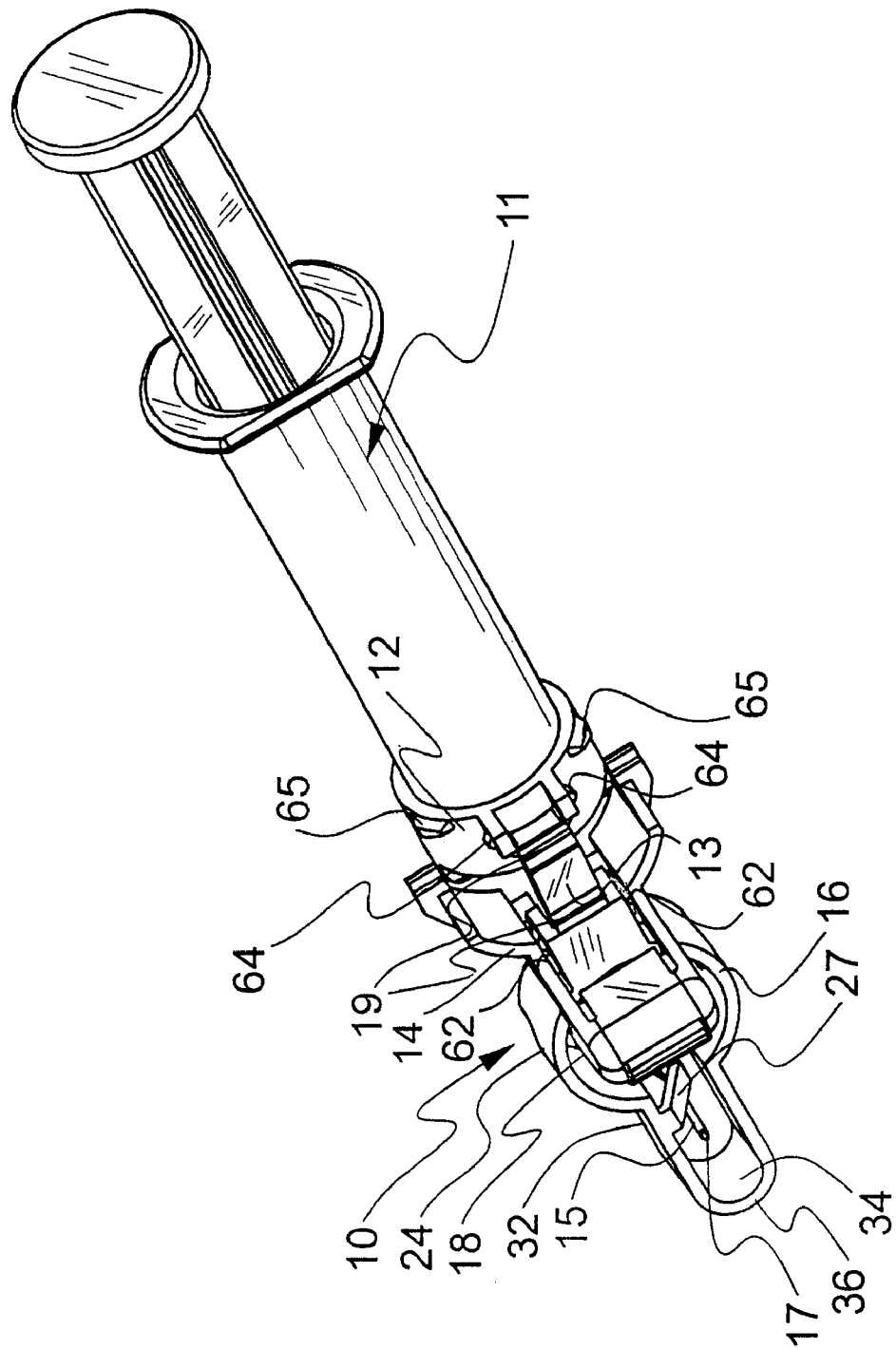
FIG. 12 is a perspective view of another embodiment of the medical needle shield apparatus showing a latch and catch system for releasably retaining the medical needle shield apparatus in a retracted position.

Referring to FIGS. 7 and 12, collar 12 includes a pair of latches 64 disposed for engagement with a corresponding pair of catches 62 formed with distal linkage 16. Cooperative engagement of latches 64 and catches 62 releasably retain safety shield 10 in the retracted position. Latches 64 have a female-type configuration for releasably receiving catches 62 male-type component part in a snap fit engagement. The releasable locking engagement provides a tactile feel and audible signal that safety shield 10 is in the retracted position. Stop 65 may be added to further impede backward travel.

To release safety shield 10 from the retracted position, a manual actuator 18 provides an engagement surface for urging safety shield 10 to the extended position and consequently disengaging catches 62 from latches 64. It is envisioned that other releasable engagements may be employed such as, for example, friction fit, interference fit, etc., that the male/female components are reversed, or, alternatively that no such releasable engagement is used.

Figure 13:
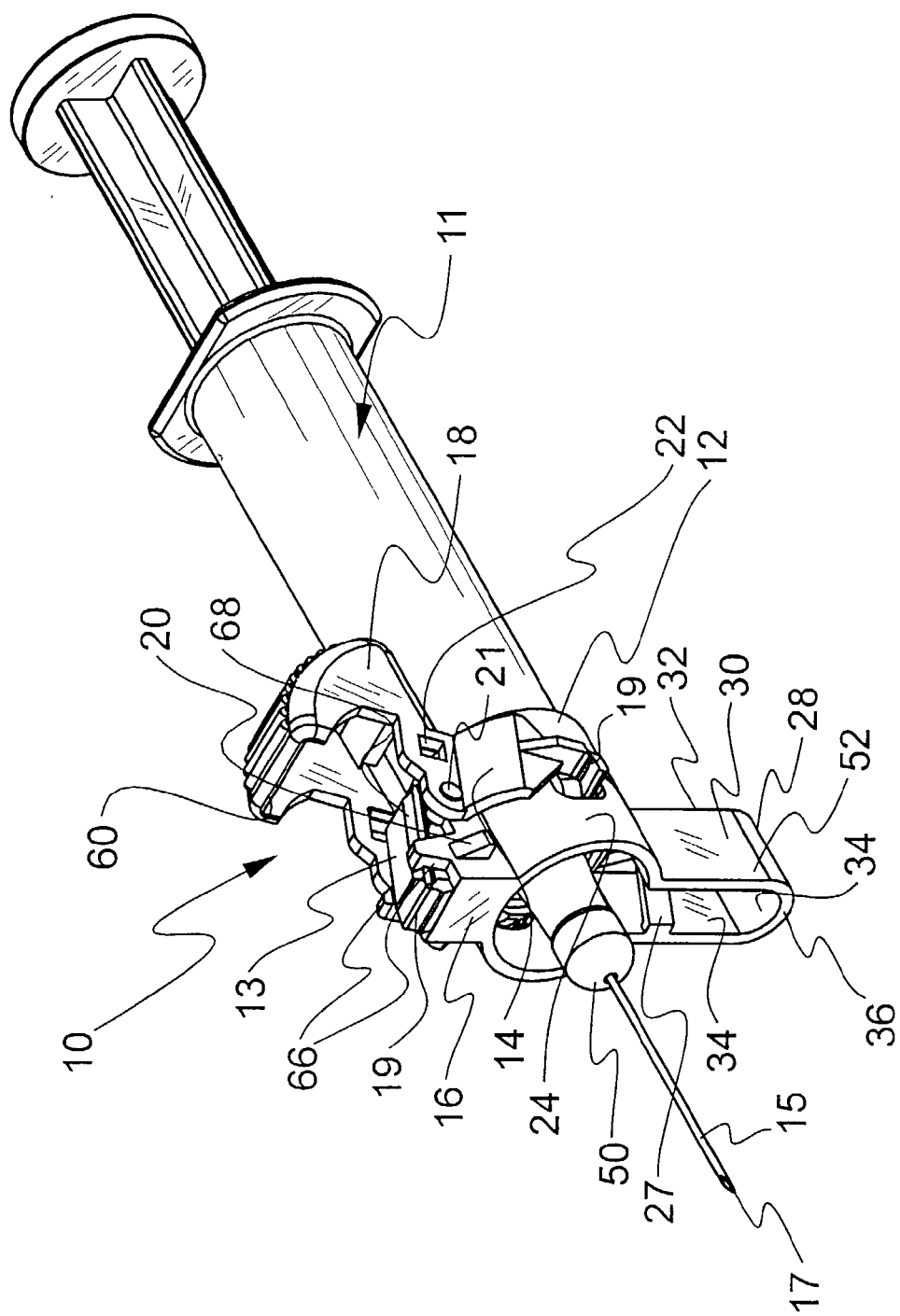
FIG. 13 is a perspective view of another embodiment showing an alternate latch and catch system for releasably retaining the medical needle shield apparatus in a retracted position.

An alternate embodiment for releasably retaining safety shield 10 in the retracted position is shown in FIG. 13, wherein distal linkage 16 includes a pair of retention latches 66 disposed for engagement with surface 68 formed with input linkage 13. Cooperative engagement of retention latches 66 and surfaces 68 releasably retains safety shield 10 in the retracted position. The releasable locking engagement provides a tactile feel and audible signal that safety shield 10 is in the retracted position.

Distal linkage 16 articulates from proximal linkage 14 and input linkage 13 in a hinged connection. It is contemplated that the hinged connection of proximal linkage 14, input linkage 13 and distal linkage 16 may be living hinges, pinned hinges, etc., or alternatively, may be movably connected by other structure, such as ball joint, etc. This configuration provides movement of distal linkage 16 relative to input linkage 13 and proximal linkage 14 facilitating extension of safety shield 10. Input linkage 13 is configured so that the shield 10 is not required to engage the needle 15 during extension of the shield 10 to the extended position. It is envisioned that one or a plurality of hinged connections may be used. It is also envisioned that input linkage 13 may also be a tether or tensile member, or similar non-rigid member. Upon engagement of manual actuator 18 with a clinician's hand, finger, etc., or a table top, etc., safety shield 10 is urged from the retracted position to the extended position for protecting a sharpened tip 17 of needle cannula 15 after a medical procedure.

Distal linkage 16 may include cylinder 24 which defines an opening 58. Opening 58 is configured for travel about needle cannula 15 to facilitate extension of safety shield 10. Cylinder 24 and opening 58 provide a cavity to accommodate needle cannula 15 such that linkages 13, 14 and 16 uniformly extend from the retracted position to the extended position via one handed operation. This configuration advantageously maintains safety shield 10 in orientation relative to needle cannula 15 during extension thereof. It is contemplated that cylinder 24 may have alternative configurations, such as, for example, rectangular, elliptical, polygonal, etc., or cylinder 24 may have various dimensions, according to the requirements of a particular medical needle application. Cylinder 24 is not required so long as opening 58 provides sufficient clearance for needle cannula 15 or any other desired syringe features.

Manipulable actuator 18 may include a surface 60, as shown in FIGS. 1, 3, 7, 8 and 10, for retaining the needle 15 when the shield 10 is fully extended. It is contemplated that surface 60 may have other configurations such as, for example, arcuate walls etc., or alternatively, may define a larger or smaller opening, according to the requirements of a particular medical needle application.

A nose portion 28 of distal linkage 16 projects from opening 58 of cylinder 24 and is in communication therewith via channel 36. Nose portion 28 includes side walls 30 and base 32 that define a cavity 34. Cavity 34 is configured for disposal of needle cannula 15 when safety shield 10 is in the extended position. Base 32 extends from cylinder 24 to the distal end of nose portion 28. Channel 36 connects opening 58 and cavity 34 facilitating extension of safety shield 10.

As linkages 13, 14 and 16 extend about needle cannula 15, cylinder 24 travels about needle cannula 15. Needle cannula 15 travels through cavity 34. As safety shield 10 approaches the extended position, needle cannula 15 engages base 32. In this position, needle cannula 15 is protectively shielded by nose portion 28 and safety shield 10 is disposed in the extended position. Safety shield 10 thereby prevents hazardous exposure to needle cannula 15 and needle tip 17 thereof. This configuration advantageously protects a clinician and subject from accidental needlestick via one handed operation of safety shield 10. Base 32 may cover all or a portion of the underside surface of nose portion 28.

Distal linkage 16 may include a pair of latches 20 disposed for engagement with a corresponding pair of catches 22 formed with proximal linkage 14 to fix safety shield 10 in the extended position. Cooperative engagement of latches 20 and catches 22 unreleasably locks safety shield 10 in the extended position. Catches 22 have a female-type configuration for unreleasably receiving latches 20 male-type component part in a snap fit engagement. The unreleasable locking engagement provides a tactile feel and audible signal that safety shield 10 is in the fully extended and locked position. As safety shield 10 approaches the extended position, needle cannula 15 engages base 32.

Figure 9:
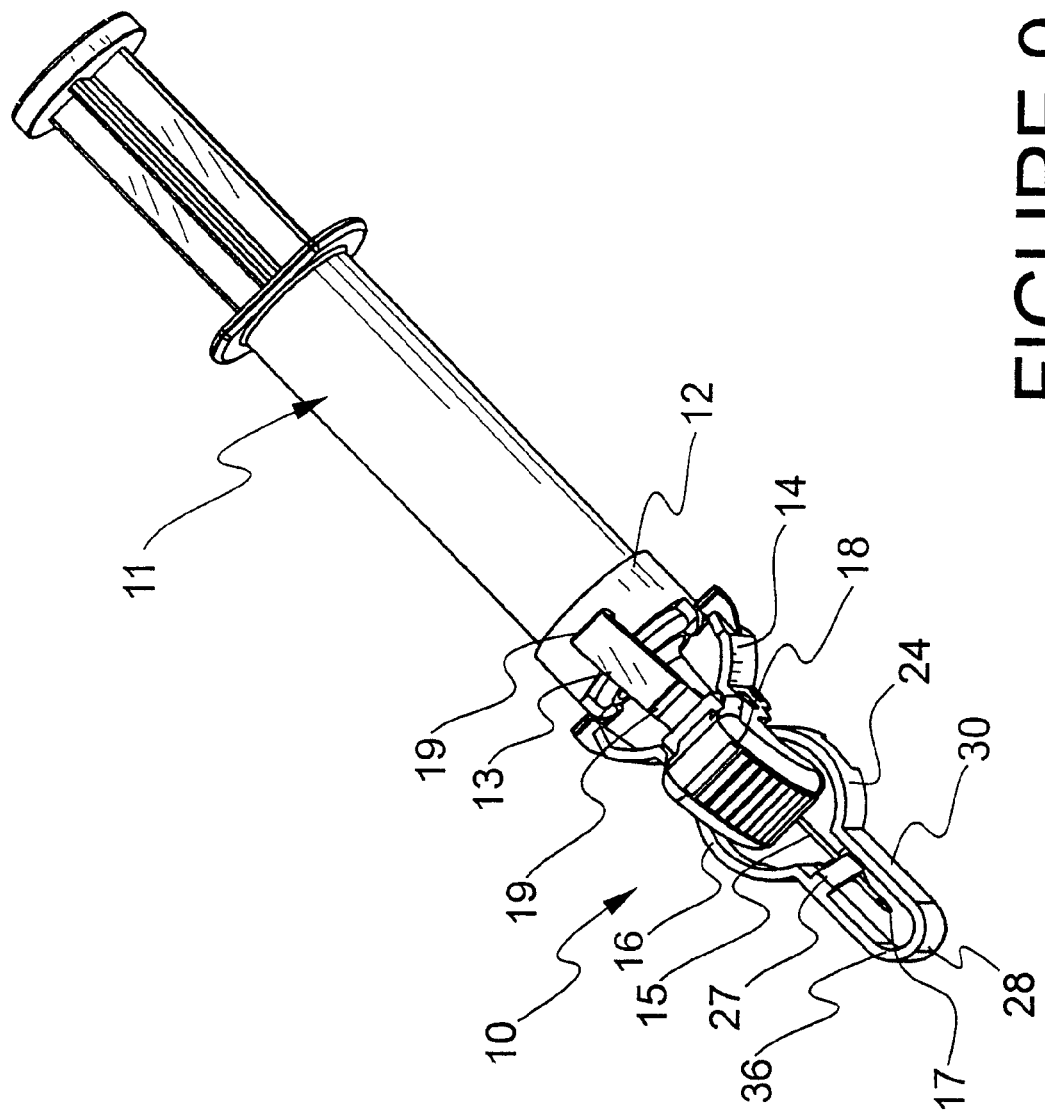
FIG. 9 is a top view of the medical needle shield apparatus illustrated in FIG. 1 showing an alternate embodiment with a needle latch for securing a medical needle to the medical needle shield apparatus in the fully extended position.

In another embodiment, linkage 16 may include a needle latch 27, as shown in FIG. 9, that engages needle cannula 15 to fix safety shield 10 in the extend position. As safety shield 10 approaches the extended position, needle cannula 15 engages base 32. Needle cannula 15 is thereby caused to engage latch 27 for retaining needle cannula 15 in cavity 34. This provides an added degree of security to the clinician and subject from accidental needle stick.

Figure 11:
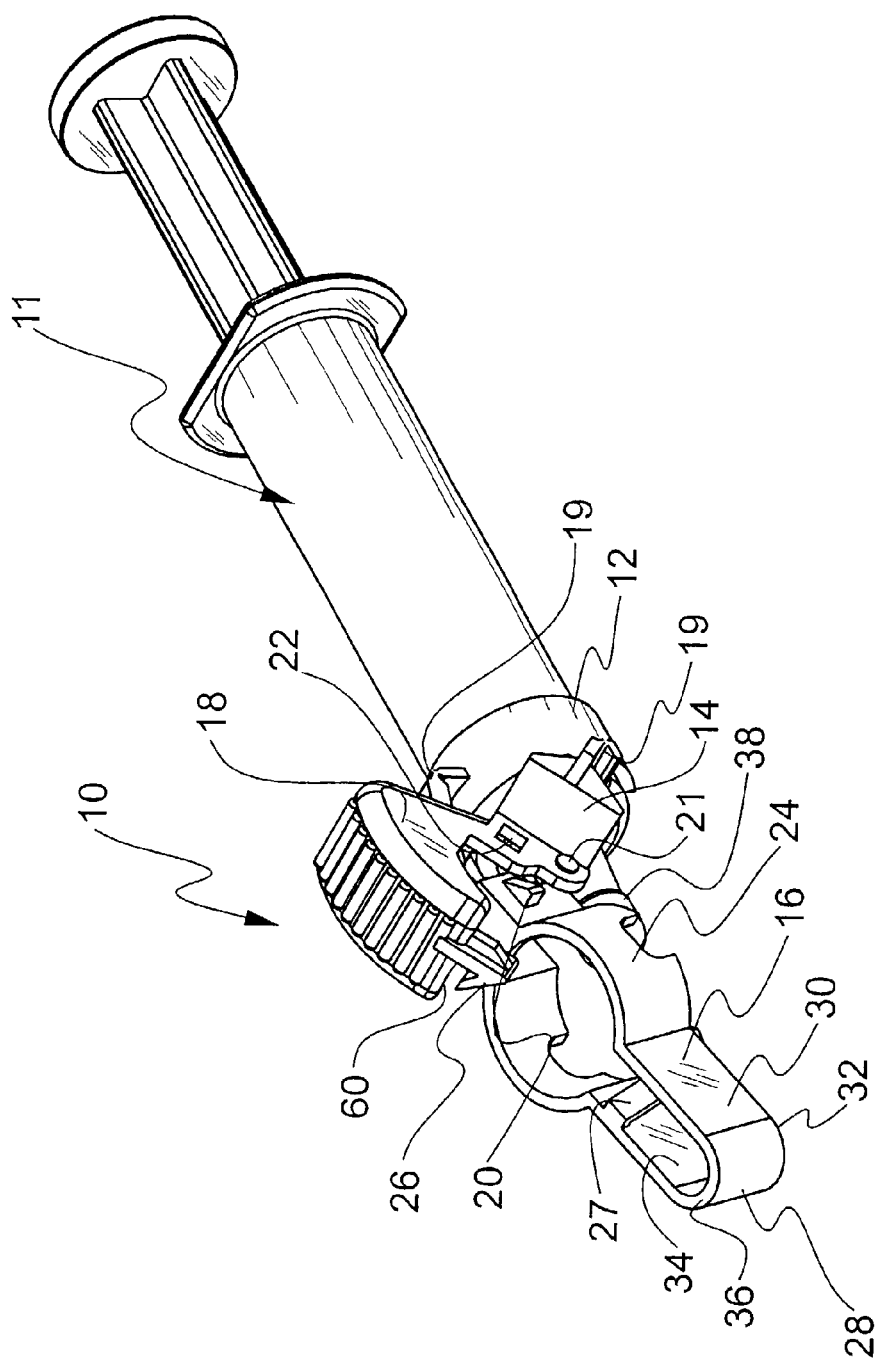
FIG. 11 is a perspective view of the medical needle shield apparatus illustrated in FIG. 1 showing another embodiment of a needle latch for securing a medical needle to the medical needle shield apparatus in the fully extended position.

In another embodiment, manipulable actuator 18 may include a barbed flap lock 26, as shown in FIG. 11, that engages needle cannula 15 to fix safety shield 10 in the extend position. It is contemplated that barbed flap lock 26 and needle latch 27 may be used in combination or singularly. As safety shield 10 approaches the extended position, needle cannula 15 engages base 32. Needle cannula 15 is thereby caused to engage lock 26 whereby lock 26 deflects about needle cannula 15. Continued manipulation of safety shield 10, via manual actuator 18, and corresponding engagement of needle cannula 15 and base 32, causes needle cannula 15 to travel over a barbed portion of lock 26 and come to rest on an opposite side thereof. Lock 26 returns to an undeflected position to non-releasably fix safety shield 10 in the extended position. This provides an added degree of security to the clinician and subject from accidental needle stick. Other lock configurations are also envisioned.

Figure 10:
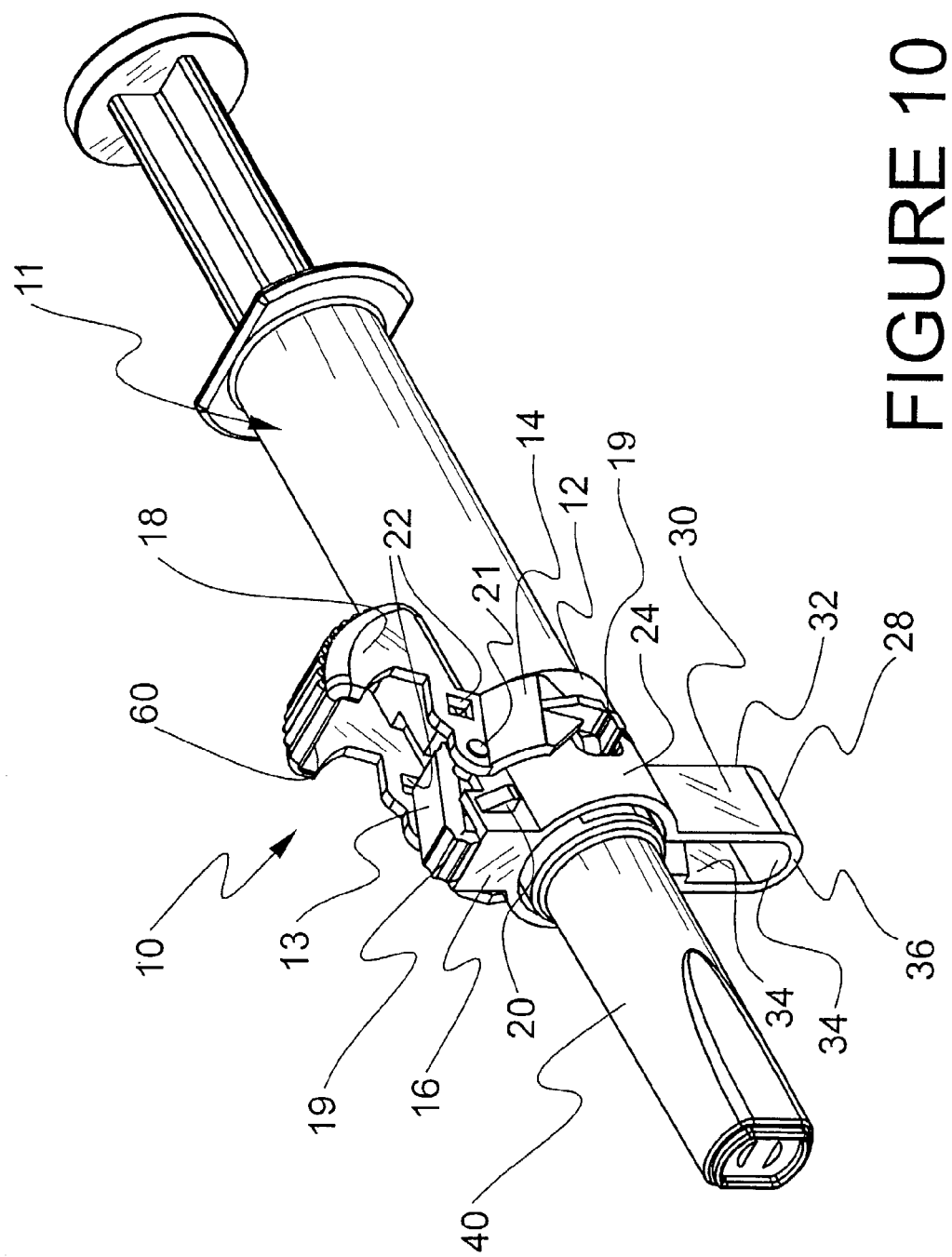
FIG. 10 is a perspective view of the medical needle shield apparatus illustrated in FIG. 1 with a needle cover attached prior to use.

In use, a medical needle apparatus employing safety shield 10 and syringe 11 are properly sterilized and otherwise prepared for storage, shipment and use. As shown in FIG. 10, a needle cover 40 is used to protect needle cannula 15. Needle cover 40 shields, prior to use and to prevent inadvertent unfolding or actuation, safety shield 10.

Safety shield 10 is in the retracted position. After completion of a medical procedure employing syringe 11, actuator 18 is manipulated such that latches 20 and catches 22 disengage. As safety shield 10 is urged from the retracted position to the extended position via one handed exertion on actuator 18, opening 58 of cylinder 24 travels about needle cannula 15.

Needle cannula 15 becomes positioned within cavity 34 through channel 36 to engage base 32. Continued pressure exerted on actuator 18 and corresponding engagement of needle cannula 15 and base 32 disposes safety shield 10 in the extended position. In the extended position, nose portion 28 shields needle tip 17 in a protective configuration to prevent hazardous exposure thereto, providing security for a clinician and subject from accidental needle stick. As safety shield 10 is disposed in the extended position and needle cannula 15 and base 32 engage, surface 42 is configured to retain needle cannula 15 and to fix safety shield 10 in the protective configuration, as discussed.

Figure 14:
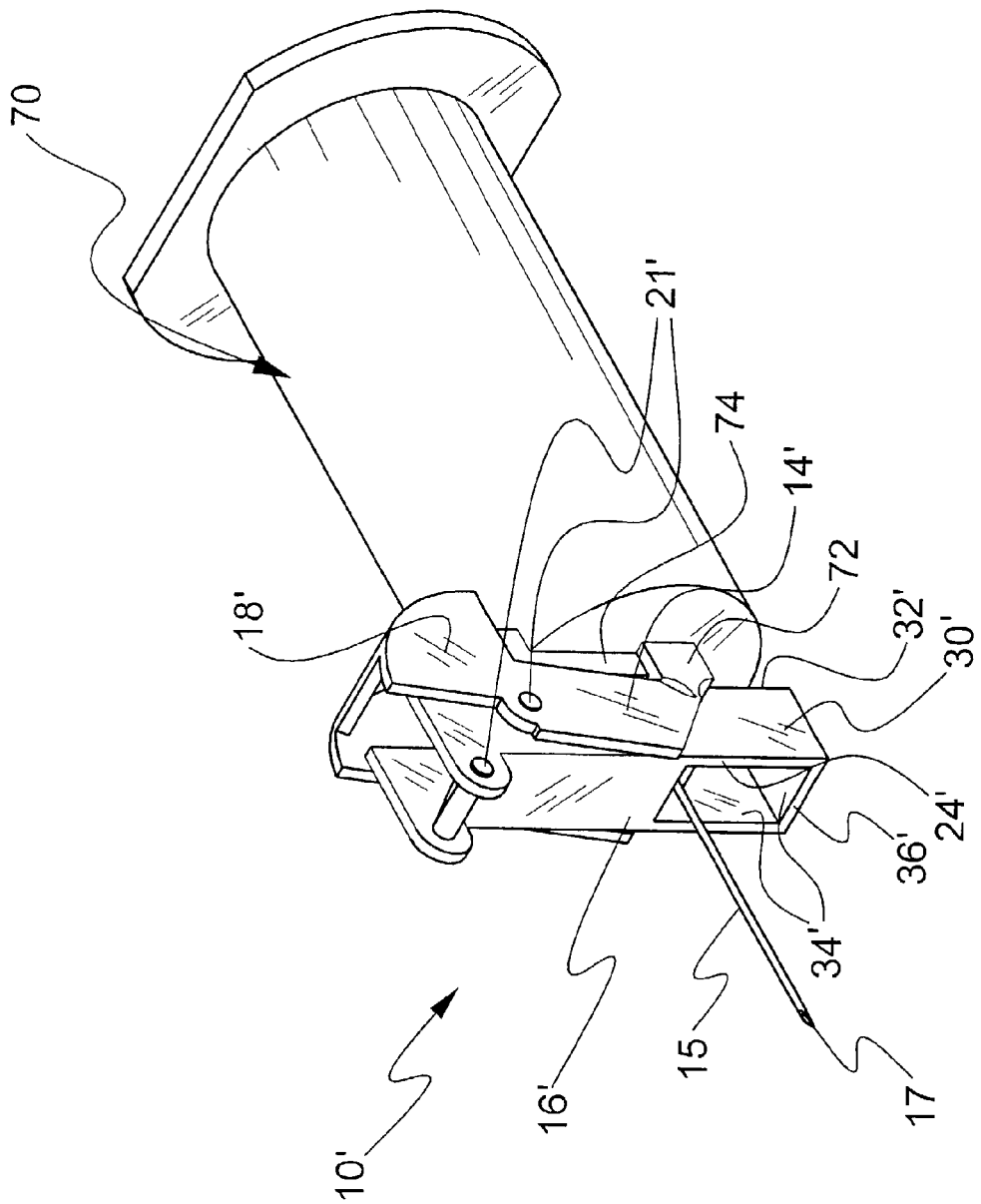
FIG. 14 is a perspective view of an alternate embodiment of the medical needle shield apparatus.
Figure 15:
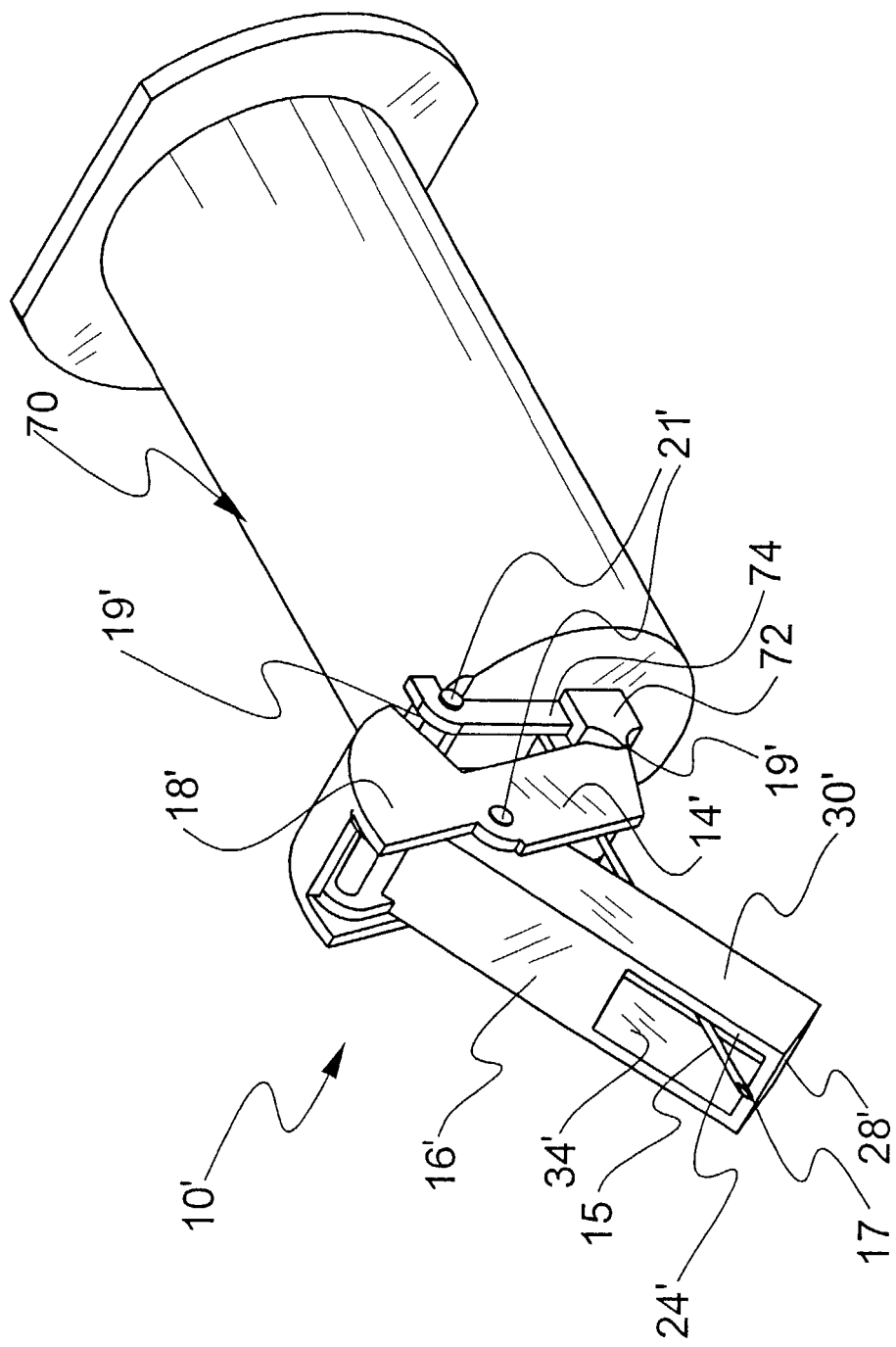
FIG. 15 is a perspective view of the medical needle shield apparatus illustrated in FIG. 14 at mid-extension.
Figure 16:
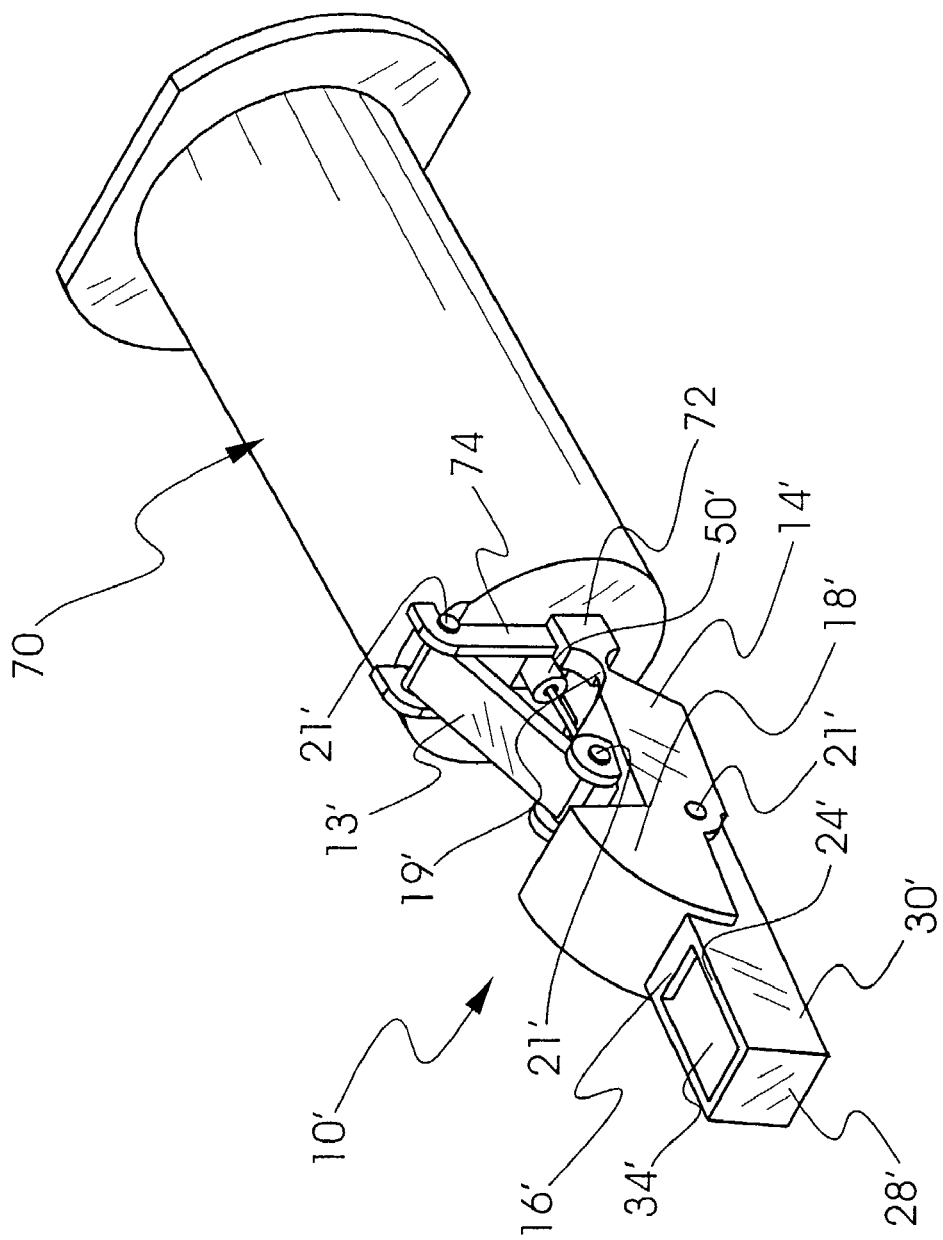
FIG. 16 is a perspective view of the medical needle shield apparatus illustrated in FIG. 14 fully extended.
Figure 17:
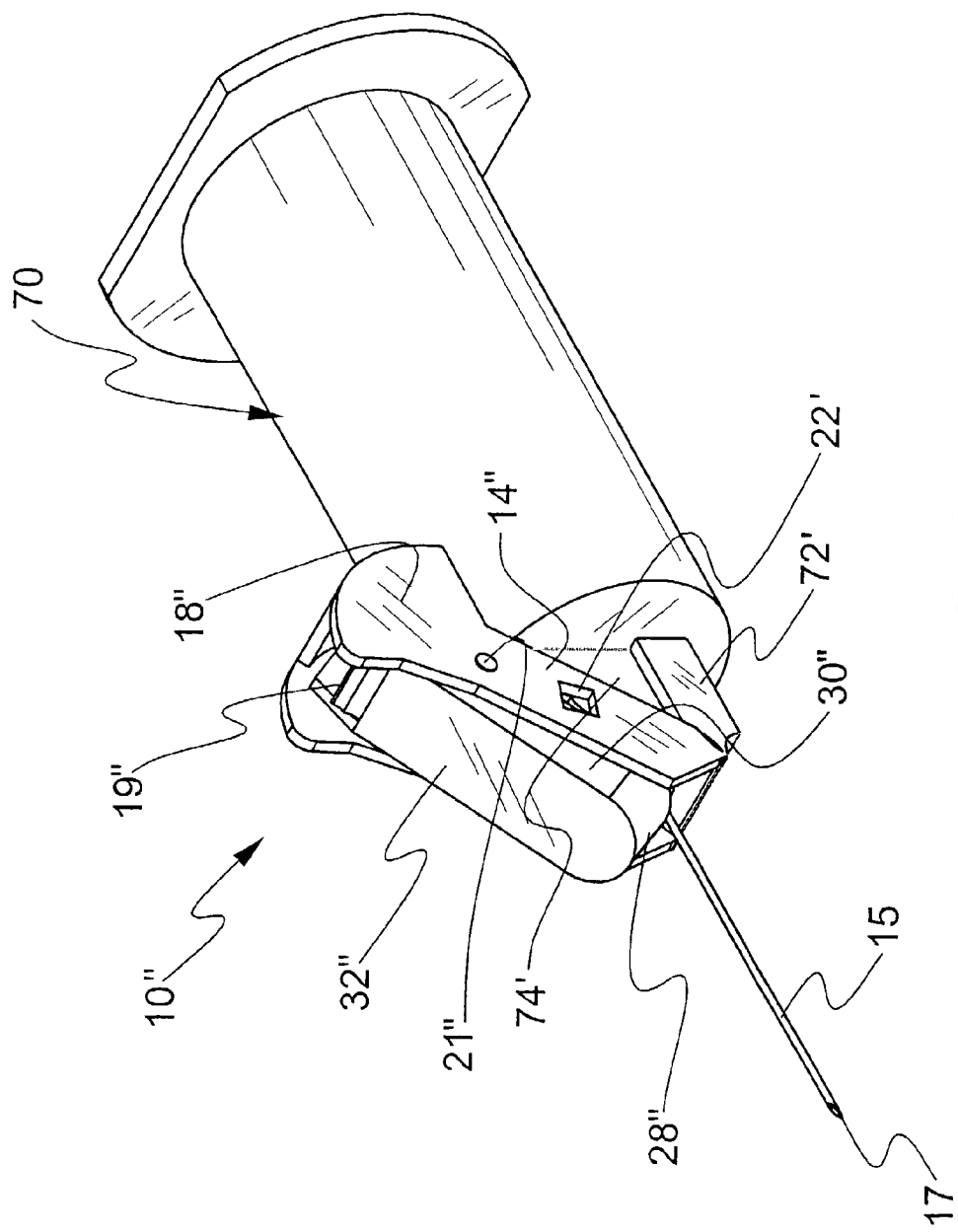
FIG. 17 is a perspective view of an alternate embodiment of the medical needle shield apparatus.

FIGS. 14–16 illustrate a medical needle device, such as, for example, a blood collection holder 70 and a safety shield 10' in a retracted position where the safety shield 10' is in a proximal position and the distal end 17 of the needle 15 is exposed prior to use. FIG. 15 shows the safety shield 10' in a mid extension position, and FIG. 16 shows the safety shield 10' in a fully extended position where the safety shield 10' extends beyond the distal end 17 of the needle 15.

Safety shield 10' includes a four-bar linkage, wherein a first segment, such as, for example, arms 72 and support 74 are configured as the fixed link with a second segment, such as, for example, proximal linkage 14', a fourth segment, such as, for example, distal linkage 16', and a third linkage, such as, for example, input linkage 13' extending therefrom. Distal linkage 16' includes an opening 24'. Opening 24' is disposed about needle cannula 15 and configured to facilitate extension of safety shield 10' between a retracted position (FIG. 14) and an extended position (FIG. 16), as will be discussed. Input linkage 13' is configured so that the shield 10' is not required to engage the needle 15 during extension of the shield 10' to the extended position.

Proximal linkage 14' is articulated to arms 72 and input linkage 13' via a hinged connection. It is contemplated that the hinged connection of proximal linkage 14' to arms 72 may be living hinges, pinned hinges, etc., or alternatively, may be movably connected by other structure, such as, ball joint, etc. This configuration provides movement of proximal linkage 14' relative to arms 72, facilitating extension of safety shield 10'. It is envisioned that one or a plurality of hinged connections may be used. Arms 72 are fixedly mounted to an outer surface of a distal end 38 of blood collection holder 70. Arms 72 may also be mounted directly to needle hub 50' or various portions of blood collection holder 70.

Input linkage 13' is articulated to support 74 and distal linkage 16' via a hinged connection. It is contemplated that the hinged connection of input linkage 13' to support 74 may be living hinges, pinned hinges, etc., or alternatively, may be movably connected by other structure, such as, ball joint, etc. This configuration provides movement of distal linkage 16' relative to support 74, facilitating extension of safety shield 10'. It is envisioned that one or a plurality of hinged connections may be used. Support 74 is fixedly mounted to an outer surface of a distal end 38 of blood collection holder 70. Support 74 may also be mounted directly to needle hub 50' or various portions of blood collection holder 70.

Distal linkage 16' articulates from proximal linkage 14' and input linkage 13' in a hinged connection. It is contemplated that the hinged connection of proximal linkage 14', input linkage 13' and distal linkage 16' may be living hinges, pinned hinges, etc., or alternatively, may be movably connected by other structure, such as ball joint, etc. This configuration provides movement of distal linkage 16' relative to input linkage 13' and proximal linkage 14' facilitating extension of safety shield 10'. It is envisioned that one or a plurality of hinged connections may be used. Upon engagement of manual actuator 18' with a clinician's hand, finger, etc., or a table top, etc., safety shield 10' is urged from the retracted position to the extended position for protecting a sharpened tip 17 of needle cannula 15 after a medical procedure.

A nose portion 28' of distal linkage 16' projects from opening 24' and is in communication therewith via channel 36'. Nose portion 28' includes side walls 30' and base 32' that define a cavity 34'. Cavity 34' is configured for disposal of needle cannula 15 when safety shield 10' is in the extended position. Base 32' extends from opening 24' to the distal end of nose portion 28'. Channel 36' connects opening 24' and cavity 34'.

As linkages 13', 14' and 16' extend about needle cannula 15, opening 24' travels about needle cannula 15. Needle cannula 15 travels through cavity 34'. As safety shield 10' approaches the extended position, needle cannula 15 engages base 32'. In this position, needle cannula 15 is protectively shielded by nose portion 28' and safety shield 10' is disposed in the extended position. Safety shield 10' thereby prevents hazardous exposure to needle cannula 15 and needle tip 17 thereof. Base 32' may cover all or a portion of the underside surface of nose portion 28'.

Figure 18:
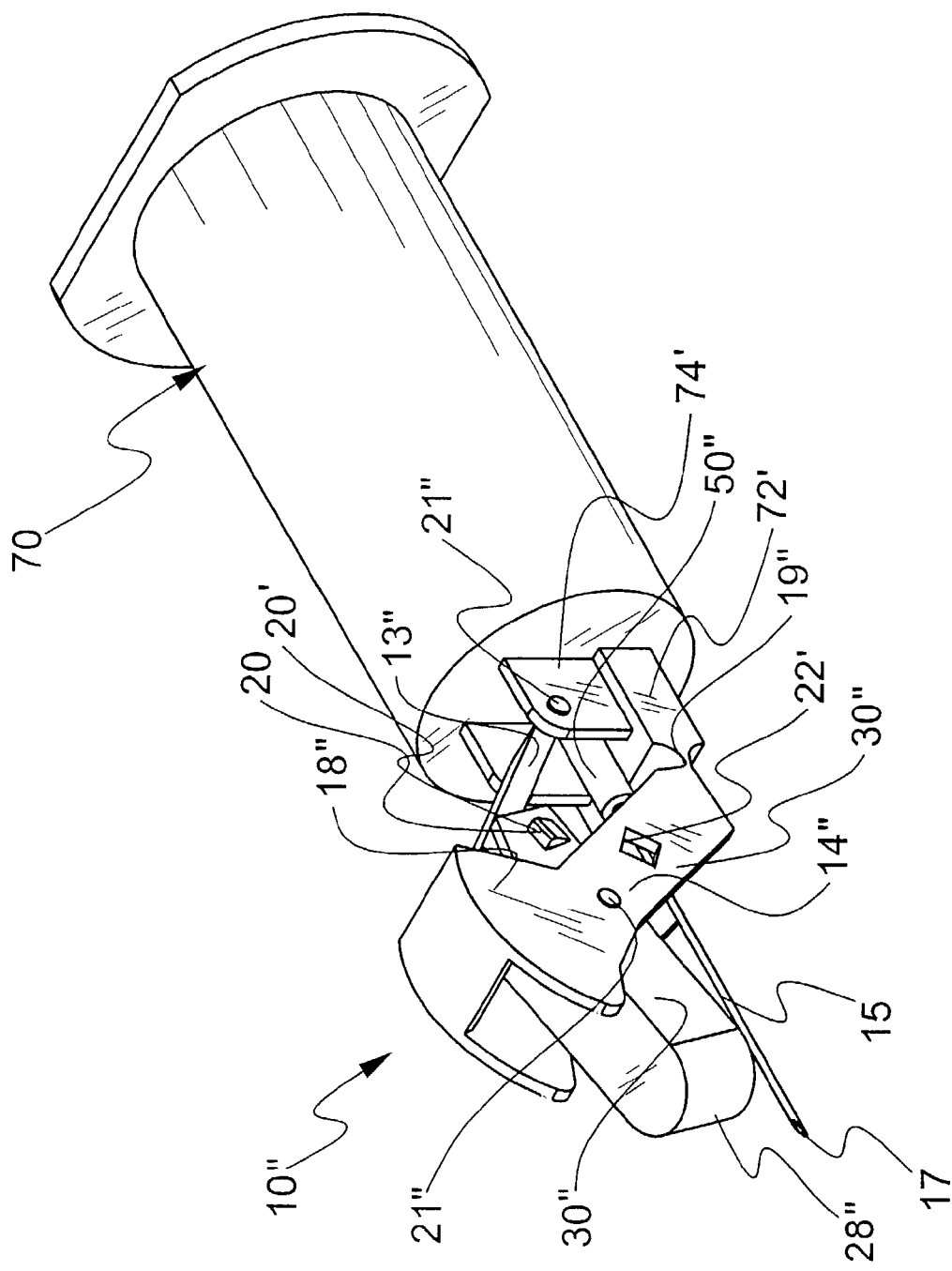
FIG. 18 is a perspective view of the medical needle shield apparatus illustrated in FIG. 17 at mid-extension.
Figure 19:
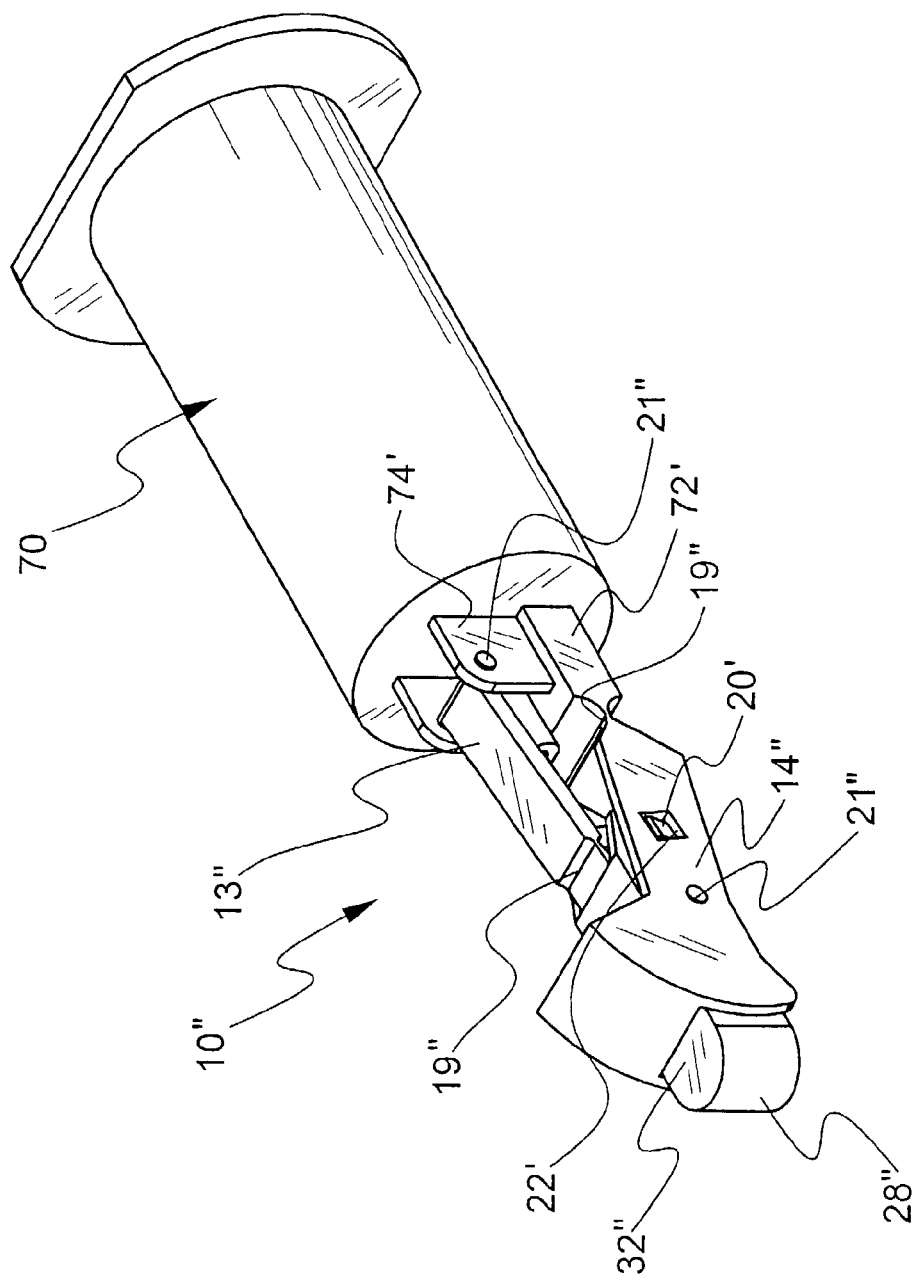
FIG. 19 is a perspective view of the medical needle shield apparatus illustrated in FIG. 17 fully extended.

FIGS. 17–22 illustrate another embodiment of a safety shield 10" for a blood collection holder 70, wherein safety shield 10" is in a retracted position and the distal end 17 of the needle 15 is exposed prior to use. FIG. 18 shows the safety shield 10" in a mid extension position, and FIG. 19 shows the safety shield 10" in a fully extended position where the safety shield 10" extends beyond the distal end 17 of the needle 15 with linkage 16" being the distal segment.

Safety shield 10" includes a four-bar linkage, wherein a first segment, such as, for example, arms 72' and support 74' are configured as the fixed link with a second segment, such as, for example, proximal linkage 14", a fourth segment, such as, for example, distal linkage 16", and a third segment, such as, for example, input linkage 13" extending therefrom. Input linkage 13" is configured so that the shield 10" is not required to engage the needle 15 during extension of the shield 10" to the extended position.

Proximal linkage 14" is articulated to arms 72' and input linkage 13" via a hinged connection. It is contemplated that the hinged connection of proximal linkage 14" to arms 72' may be living hinges, pinned hinges, etc., or alternatively, may be movably connected by other structure, such as, ball joint, etc. This configuration provides movement of proximal linkage 14" relative to arms 72', facilitating extension of safety shield 10'. It is envisioned that one or a plurality of hinged connections may be used. Arms 72' are fixedly mounted to an outer surface of a distal end 38' of blood collection holder 70. Arms 72' may also be mounted directly to needle hub 50' or various portions of blood collection holder 70.

Input linkage 13" is articulated to support 74' and distal linkage 16" via a hinged connection. It is contemplated that the hinged connection of input linkage 13" to support 74' may be living hinges, pinned hinges, etc., or alternatively, may be movably connected by other structure, such as, ball joint, etc. This configuration provides movement of distal linkage 16" relative to support 74', facilitating extension of safety shield 10". It is envisioned that one or a plurality of hinged connections may be used. Support 74' is fixedly mounted to an outer surface of a distal end 38' of blood collection holder 70. Support 74' may also be mounted directly to needle hub 50' or various portions of blood collection holder 70.

Distal linkage 16" articulates from proximal linkage 14" and input linkage 13" in a hinged connection. It is contemplated that the hinged connection of proximal linkage 14", input linkage 13" and distal linkage 16" may be living hinges, pinned hinges, etc., or alternatively, may be movably connected by other structure, such as ball joint, etc. This configuration provides movement of distal linkage 16" relative to input linkage 13" and proximal linkage 14" facilitating extension of safety shield 10". It is envisioned that one or a plurality of hinged connections may be used. Upon engagement of manual actuator 18" with a clinician's hand, finger, etc., or a table top, etc., safety shield 10' is urged from the retracted position to the extended position for protecting a sharpened tip 17 of needle cannula 15 after a medical procedure.

A nose portion 28" of distal linkage 16" is in communication with channel 36". Nose portion 28" includes side walls 30" and base 32" that define a cavity 34". Cavity 34" is configured for disposal of needle cannula 15 when safety shield 10" is in the extended position. Base 32" extends to the distal end of nose portion 28".

As linkages 13", 14" and 16" extend about needle cannula 15, needle cannula 15 travels through cavity 34". As safety shield 10" approaches the extended position, needle cannula 15 engages surface 42". In this position, needle cannula 15 is protectively shielded by nose portion 28" and safety shield 10" is disposed in the extended position. Safety shield 10" thereby prevents hazardous exposure to needle cannula 15 and needle tip 17 thereof. Base 32" may cover all or a portion of the top surface of nose portion 28".

Distal linkage 16" may include a pair of latches 20' disposed for engagement with a corresponding pair of catches 22' formed with proximal linkage 14" to fix safety shield 10" in the extended position. Cooperative engagement of latches 20' and catches 22' unreleasably locks safety shield 10" in the extended position. Catches 22' have a female-type configuration for unreleasably receiving latches 20' male-type component part in a snap fit engagement. The unreleasable locking engagement provides a tactile feel and audible signal that safety shield 10" is in the fully extended and locked position. As safety shield 10" approaches the extended position, needle cannula 15 engages surface 42".

Figure 20:
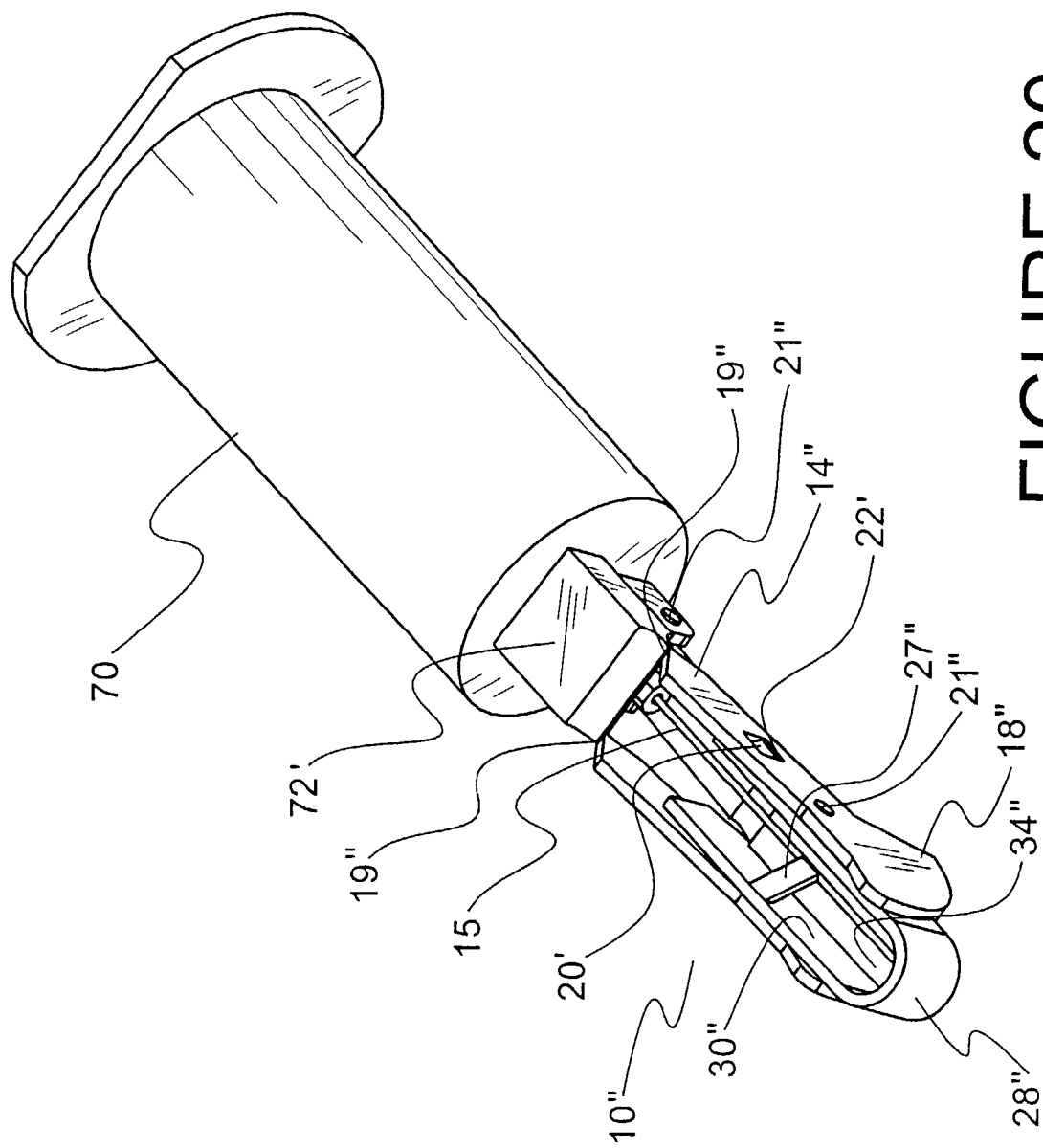
FIG. 20 is a bottom view of the medical needle shield apparatus illustrated in FIG. 17 showing an alternate embodiment with a needle latch for securing a medical needle to the medical needle shield apparatus in the fully extended position.

In another embodiment, linkage 16" may include a needle latch 27', as shown in FIG. 20, that engages needle cannula 15 to fix safety shield 10" in the extend position. As safety shield 10" approaches the extended position, needle cannula 15 engages surface 42". Needle cannula 15 is thereby caused to engage latch 27' for retaining needle cannula 15 in cavity 34". This provides an added degree of security to the clinician and subject from accidental needle stick.

Figure 21:
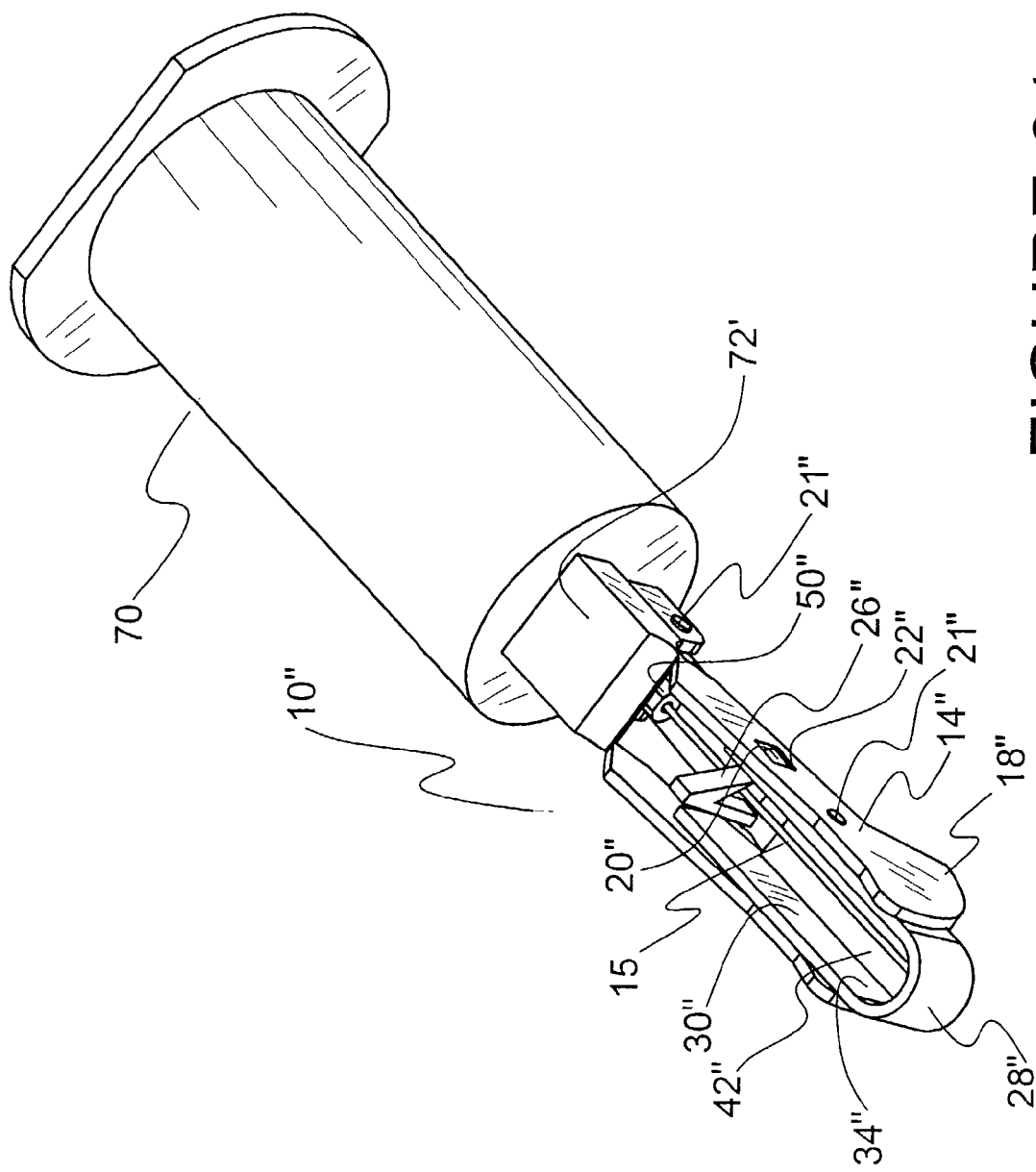
FIG. 21 is a bottom view of the medical needle shield apparatus illustrated in FIG. 17 showing another embodiment of a needle latch for securing a medical needle to the medical needle shield apparatus in the fully extended position.
Figure 22:
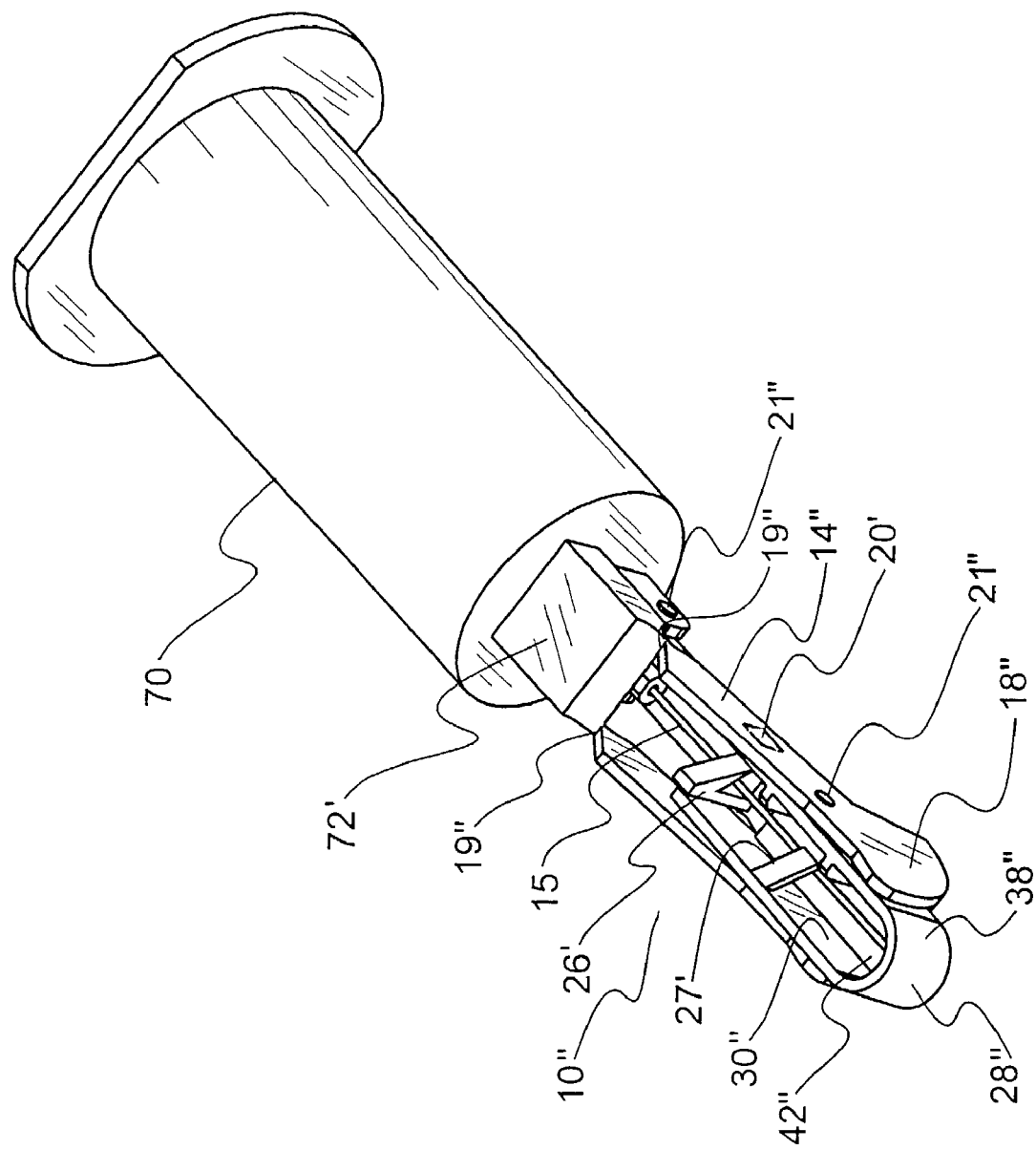
FIG. 22 is a bottom view of the medical needle shield apparatus illustrated in FIG. 17 showing an alternate embodiment with multiple needle latches for securing a medical needle to the medical needle shield apparatus in the fully extended position.
Figure 23:
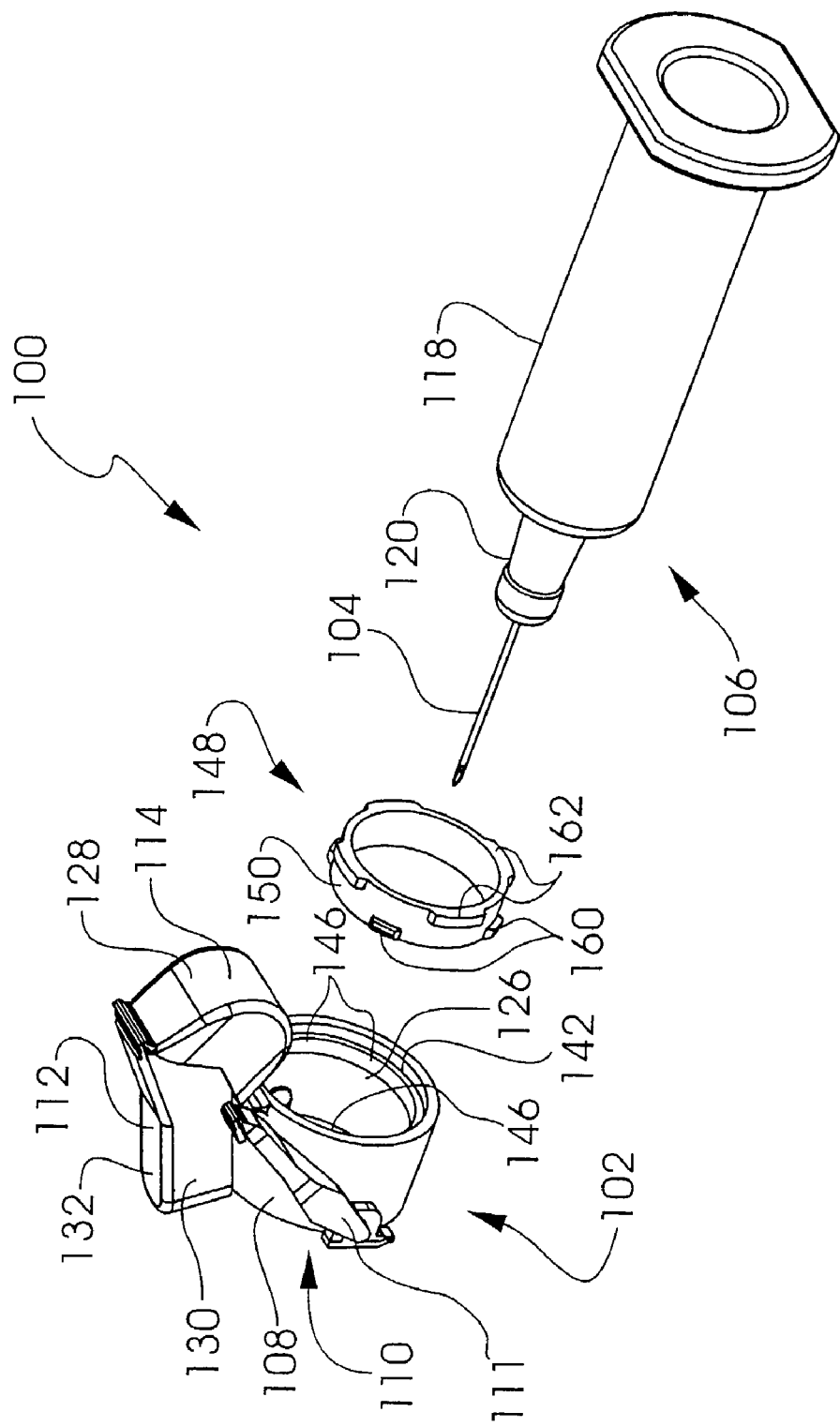
FIG. 23 is an exploded perspective view of an alternate embodiment of a medical needle shield apparatus, in accordance with the principles of the present disclosure.
Figure 24:
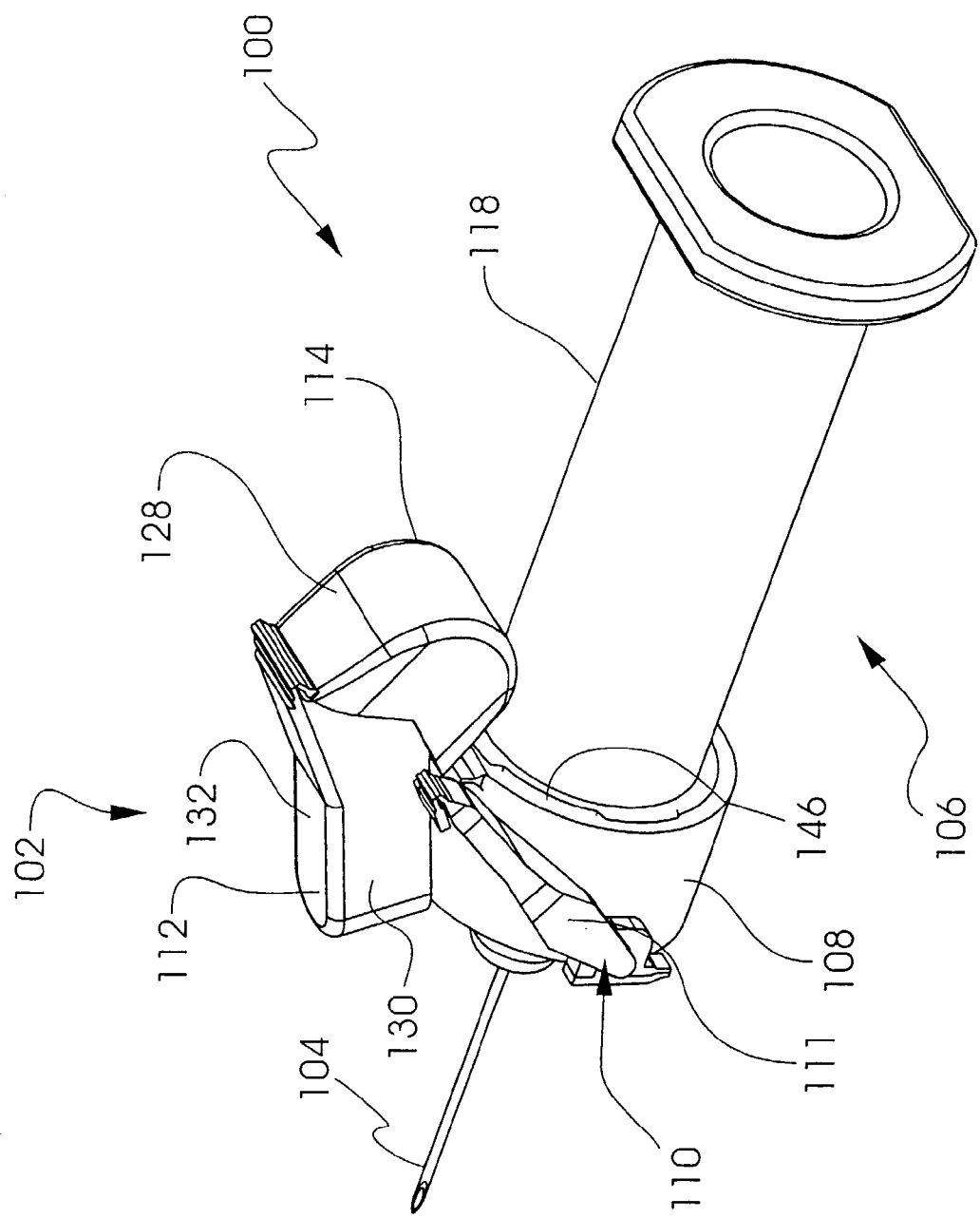
FIG. 24 is a perspective view of the medical needle shield apparatus shown in FIG. 23.
Figure 25:
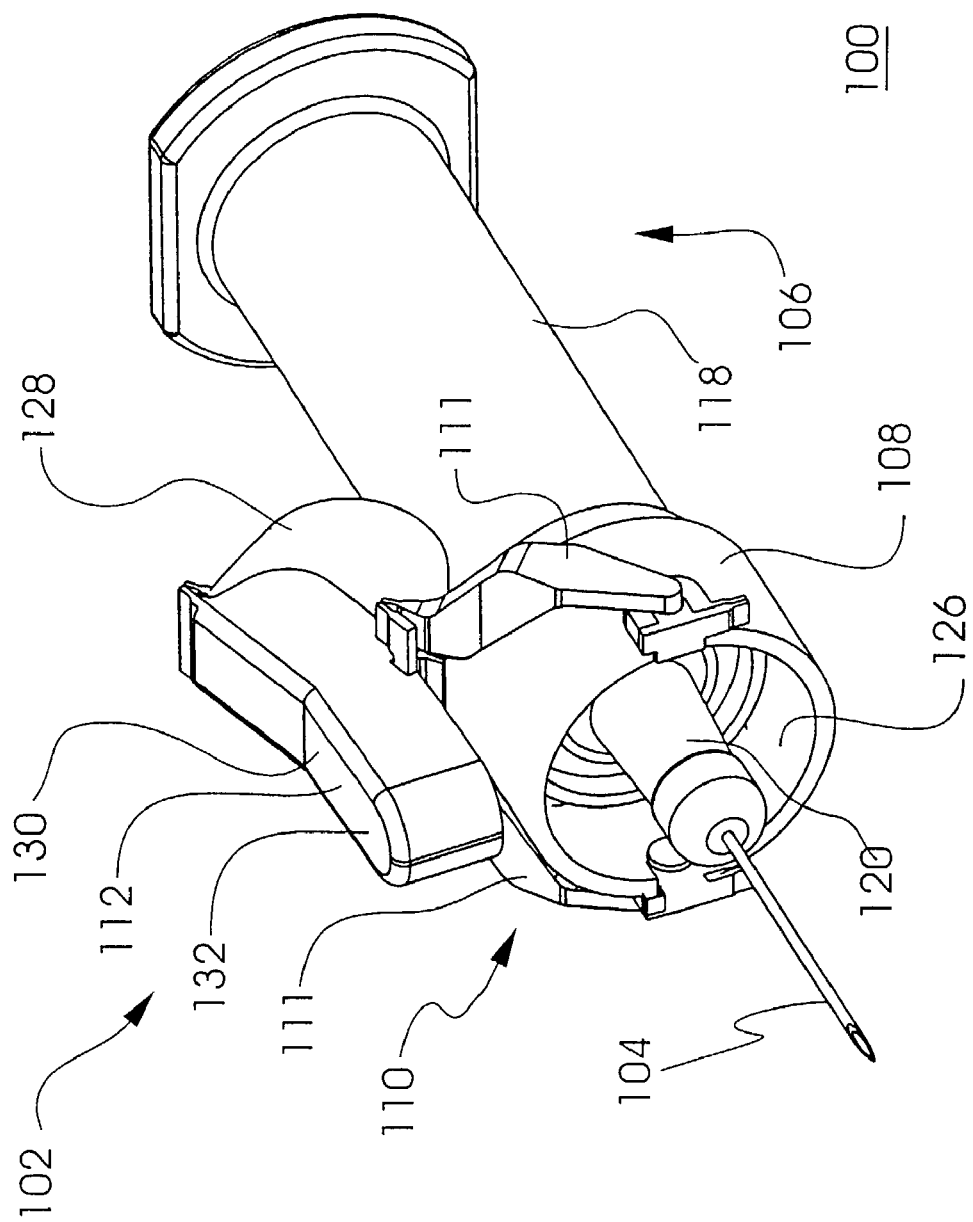
FIG. 25 is an alternate perspective view of the medical needle shield apparatus shown in FIG. 23 in a retracted position.
Figure 26:
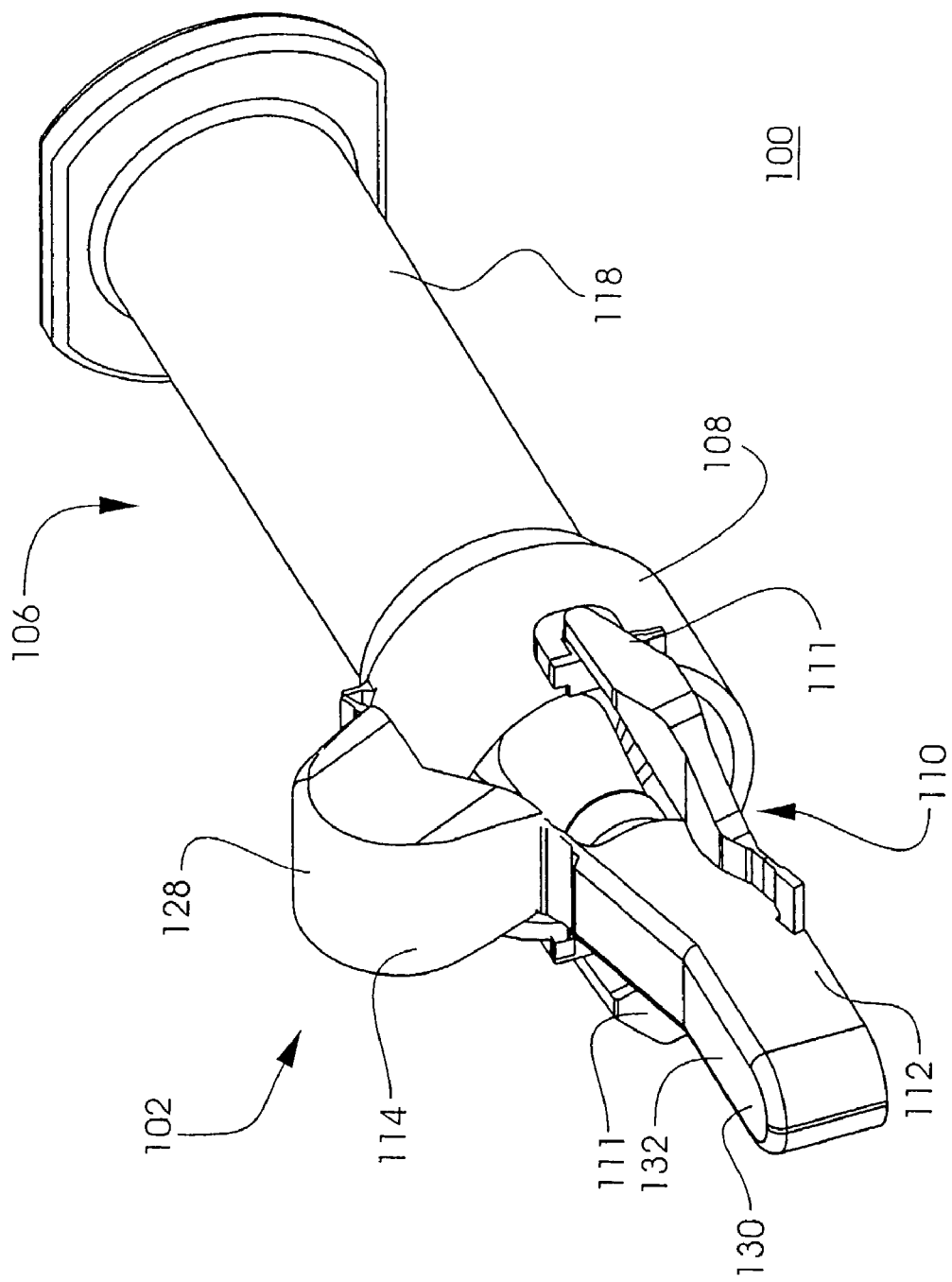
FIG. 26 is an alternate perspective view of the medical needle shield apparatus shown in FIG. 23 in the extended position.

In another embodiment, manipulable actuator 18" may include a barbed flap lock 26', as shown in FIG. 21, that engages needle cannula 15 to fix safety shield 10" in the extend position. It is contemplated that barbed flap lock 26' and needle latch 27' may be used in combination (as shown in FIG. 22) or singularly. As safety shield 10" approaches the extended position, needle cannula 15 engages surface 42". Needle cannula 15 is thereby caused to engage lock 26' whereby lock 26' deflects about needle cannula 15. Continued manipulation of safety shield 10", via manual actuator 18", and corresponding engagement of needle cannula 15 and surface 42", causes needle cannula 15 to travel over a barbed portion of lock 26' and come to rest on an opposite side thereof. Lock 26' returns to an undeflected position to non-releasably fix safety shield 10" in the extended position. This provides an added degree of security to the clinician and subject from accidental needle stick. Other lock configurations are also envisioned.

Referring to FIGS. 23–28, there is illustrated a medical needle shield apparatus 100, similar to those described and methods of use, in accordance with the principles of the present disclosure. Medical needle shield apparatus 100 includes a shield 102 extensible from a retracted position (FIG. 24) to an extended position (FIG. 26) for enclosing a distal end of a needle 104 extending from a medical needle device 106.

Shield 102 includes a first segment, such as, for example, collar 108 mounted to medical needle device 106. A second segment, such as, for example, manual actuator 128 and a third segment, such as, for example, proximal segment 110 articulates from collar 108. Manual actuator 128 includes an engagement surface 114. Engagement surface 114 is engageable to urge shield 102 from the retracted position such that manual actuator 128 and proximal segment 110 cooperate to extend shield 102 to the extended position. A fourth segment such as, for example, distal segment 112 articulates from manual actuator 128 and proximal segment 110. Distal segment 112 is configured to enclose the distal end of needle 104. This configuration advantageously provides a reliable structure that prevents hazardous exposure to needle 104.

Shield 102 is monolithically formed by fabrication techniques such as, molding, etc. It is contemplated that the components of shield 102 may be integrally assembled via snaps, slips, adhesive, etc. It is further contemplated that shield 102 may include one or a plurality of segments. The components of the medical needle shield apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

Collar 108 is cylindrical and circumferentially disposed about medical needle device 106. It is envisioned that collar 108 may have various cross-sectional configurations corresponding to the configuration of medical needle device 106. Medical needle device 106 includes, for example, a syringe 118. Syringe 118 has needle cannula 104 extending therefrom via a needle hub 120.

Manual actuator 128 is articulated from collar 108 via a living hinge connection. This configuration facilitates movement of manual actuator 128 relative to collar 108. It is envisioned that manual actuator may also be connected via pinned hinges, ball-joint, etc.

Manual actuator 128 includes engagement surface 114. Engagement surface 114 has an outer arcuate surface configured for engagement with a clinician's hand, tabletop, etc. Such engagement facilitates extension of shield 102 via cooperation with proximal segment 110, from the retracted position to the extended position. It is contemplated that engagement surface 114 may include ridges, grooves, etc., that enhance gripping thereof. It is further contemplated that engagement surface 114 may have other configurations such as, for example, planar, etc. that facilitate extension of shield 102.

Figure 27:
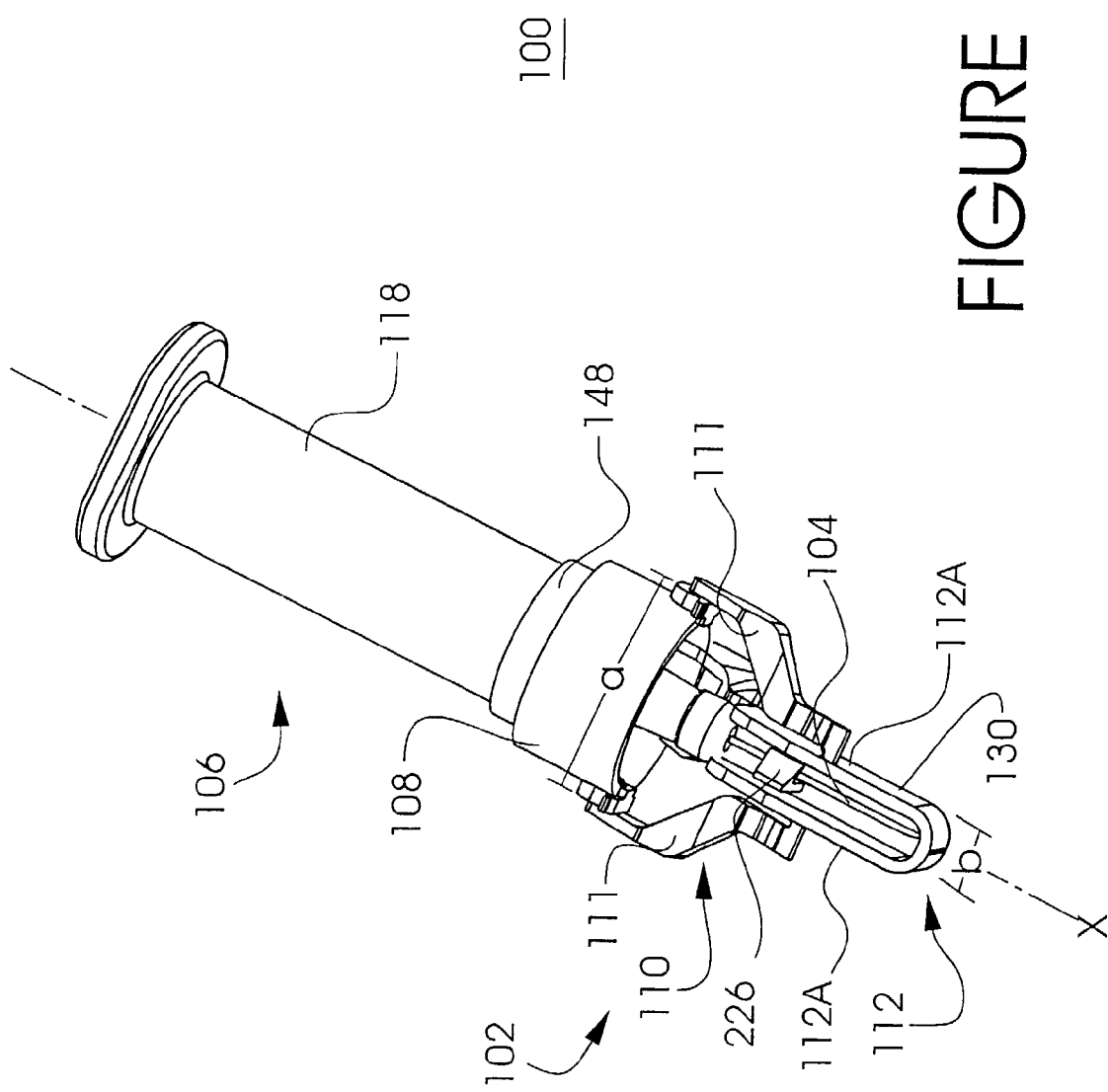
FIG. 27 is an alternate perspective view of the medical needle shield apparatus shown in FIG. 23 in the extended position.
Figure 28:
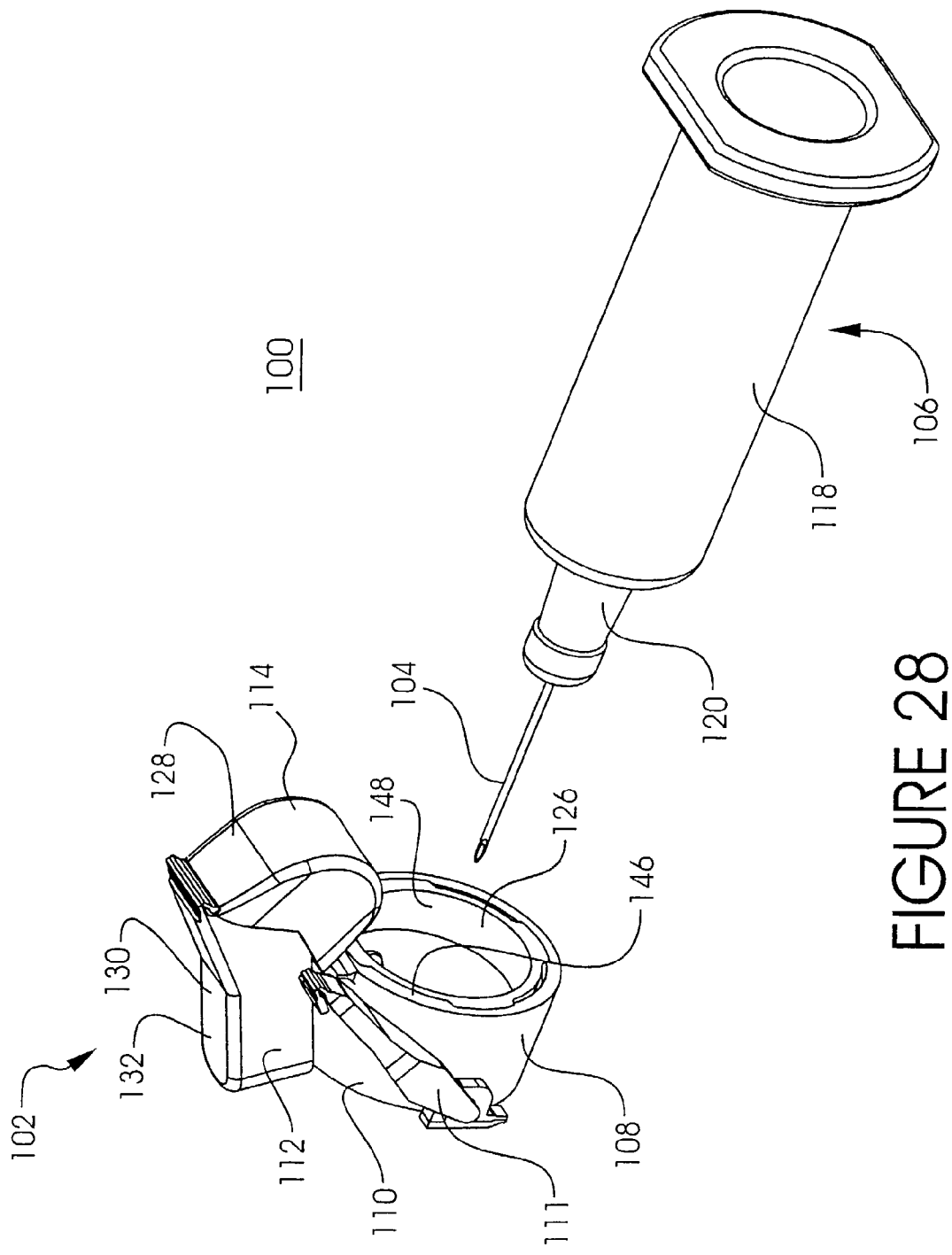
FIG. 28 is a partially exploded perspective view of the medical needle shield apparatus shown in FIG. 23.

Proximal segment 110 is articulated from collar 108 via a pair of axially extending arms 111. Arms 111 extend from collar 108 via a hinged connection. It is contemplated that such hinged connection may include living hinges, pinned hinges, balljoint, etc. Arms 111 extend and connect with lateral portions 112A, as shown in FIG. 27, of distal segment 112. Proximal segment 110 is configured such that engagement of needle 104 with shield 102 is not required to facilitate extension of shield 102.

Arms 111 extend in a corresponding configuration between collar 108 and distal segment 112. At collar 108, arms 111 extend a greater transverse dimension a, as shown in FIG. 27, relative to a longitudinal axis x of needle 104, to accommodate connection thereto. At distal segment 112, arms 111 converge to a narrower dimension b to accommodate connection to distal segment 112. As manual actuator 128 is engaged to urge shield to the extended position, arms 111 rotate, relative to longitudinal axis x of needle 104, in a counter-clockwise direction. This extension, as facilitated cooperatively by manual actuator 128 and proximal segment 110, advantageously disposes distal segment 112 in a position to substantially enclose the distal end of needle 104 without requiring engagement of shield 102 with needle 104 thereby facilitating extension of shield 102. It is envisioned that arms 111 may extend between collar 108 and distal segment 112 in distinct configurations. It is further envisioned that one or a plurality of arms 111 may be employed.

Distal segment 112 articulates from proximal segment 110 and manual actuator 128 via hinged connection. Distal segment 112 is connected to manual actuator 128 adjacent a proximal end thereof via a living hinge connection. Manual actuator 128 is attached to distal segment 112 such that manipulation of manual actuator 128 causes direct axial extension of distal segment 112 relative to collar 108. Arms 111 are connected to distal segment 112 at lateral sides of a nose portion 130 at a mid-portion thereof. As arms 111 rotate counter-clockwise, nose portion 130 moves into a position that substantially encloses the distal end of needle 104 without requiring engagement with needle 104 to facilitate extension of shield 102.

Referring to FIG. 27, distal segment 112 includes a barbed flap lock 226 that engages needle 104 to fix shield 102 in the extended position. Barbed flap lock 226 engages and deflects about needle 104. Barbed flap lock 226 comes to rest in an undeflected position to non-releasably fix shield 102 in the extended position. It is envisioned that barbed flap back 226 may be releasable or that other lock configurations may be used. Distal segment 112 includes nose portion 130 having a planar surface 132. In the extended position of shield 102, nose portion 130 substantially encloses the distal end of needle 104 in cooperation with planar surface 132. It is contemplated that manual actuator 128 and proximal segment 110 may be connected at various positions of distal segment 112 to facilitate extension of shield 102.

Collar 108 has an inner surface 142 that defines a collar cavity 126. Inner surface 142 includes at least one first interlock, such as a plurality of collar stops 146 that project radially inward. Collar stops 146 are uniformly raised within collar cavity 126 for engagement with a second cylinder, such as, for example, a mounting ring 148. This configuration facilitates mounting of shield 102 with syringe 118. It is envisioned that one or a plurality of collar stops 146 may be used. It is further envisioned that collar stops 146 may be raised or project in a non-uniform manner, such as, for example, staggered, offset, undulating, etc. to include an annular ring. It is contemplated that collar stops 146 may include bands, rings, grooves, etc.

Mounting ring 148 is configured for mounting with syringe 118. This configuration advantageously facilitates mounting shield 102 with syringe 118. Mounting ring 148 has an outer surface 150 that includes at least one second interlock, such as a plurality of radially outward projecting proximal stops 162 and a plurality of radially outward projecting distal stops 160. Proximal stops 162 and distal stops 160 are equidistantly disposed, circumferentially, about outer surface 150. Proximal stops 162 and distal stops 160 are uniformly raised from outer surface 150 for disposal within collar cavity 126. It is contemplated that one or a plurality of stops 162, 160 may be employed. It is further contemplated that stops 162, 160 may be raised or project in a non-uniform manner, such as, for example, staggered offset, undulating, etc. to include an annular ring. It is envisioned that stops 162, 160 may include bands, rings, grooves, etc. The first and second interlocks prevent movement in both proximal and axial directions. A third interlock may be added to prevent rotational movement.

Figure 29:
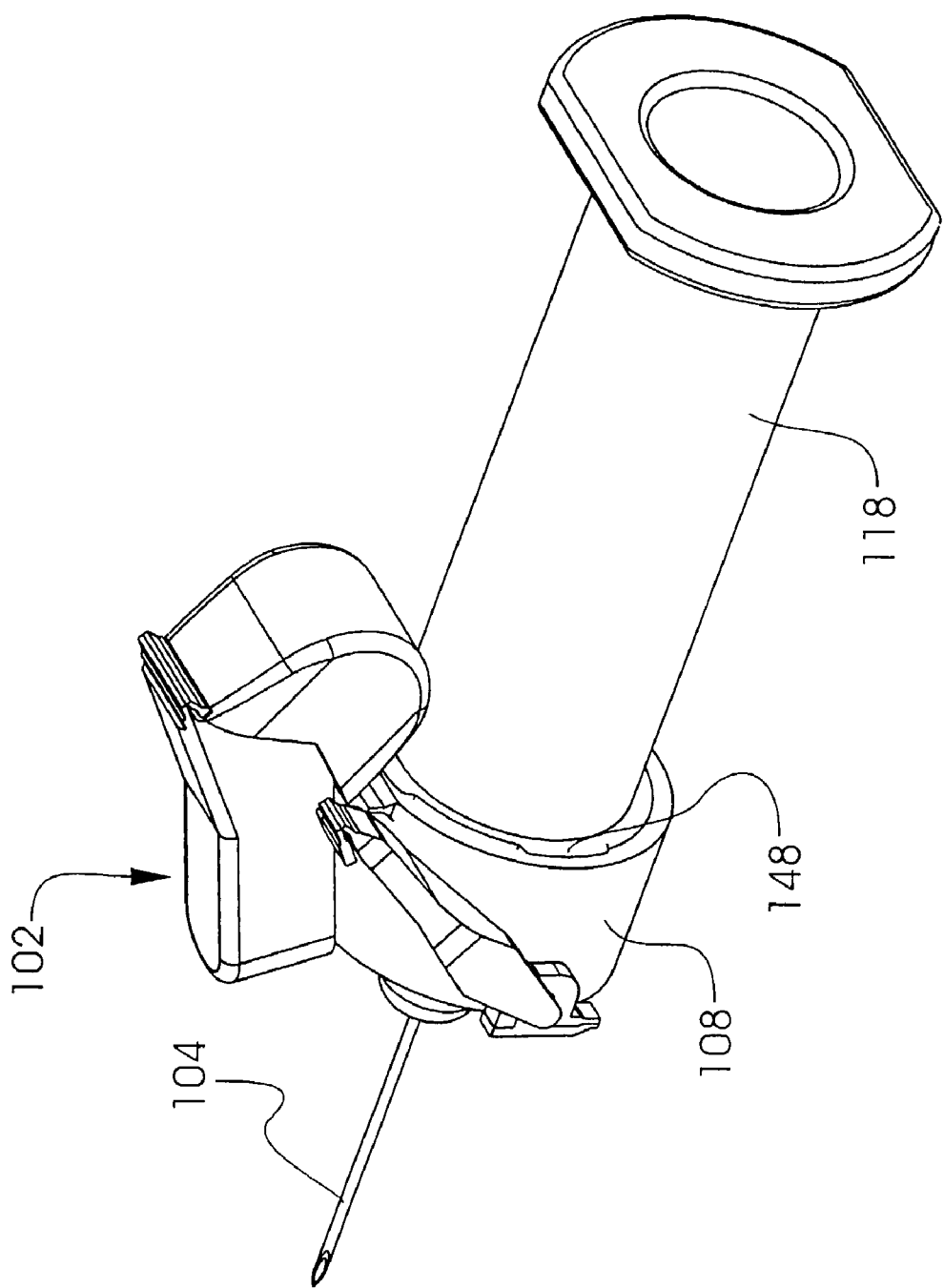
FIG. 29 is a perspective view of an alternate embodiment of the medical needle shield apparatus shown in FIG. 23.

Mounting ring 148 may be mounted to syringe 118 via an adhesive, as shown in FIG. 29, such as, for example, pressure-sensitive adhesive, ultraviolet light-activated adhesive, hot-glue adhesive, 1-part and/or 2-part adhesive, rubber cement, "super glue" type adhesives, glue stick type adhesives, air-dry adhesives, press fit, etc. It is envisioned that no mounting ring may be used. Collar 108 may be similarly mounted to syringe 118.

Collar 108 is mounted for relative rotational movement with mounting ring 148 such that outer surface 150 is disposed within collar cavity 126. Collar stops 146 are disposed adjacent to outer surface 150. Collar 108 is rotated relative to mounting ring 148 such that collar stops 146 are oriented in an interlocking arrangement with proximal stops 162 and distal stops 160. Thus, proximal stops 162 are aligned with collar stops 146 to prevent distal axial movement, relative to a longitudinal axis of syringe 118, of collar 108. Distal stops 160 are aligned with collar stops 146 to prevent proximal axial movement of collar 108.

This configuration advantageously prevents removal of shield 102 from syringe 118. Further, this configuration avoids impedance of administration of fluids via medical needle device 106, during, for example, low-angle subcutaneous injections, etc. Thus, collar 108 is rotatable relative to mounting ring 148, which is mounted to syringe 118, facilitating orientation of the needle bevel of needle cannula 104. This allows selective orientation of the needle bevel relative to shield 102 such that shield 102 does not interfere with positioning during an administration procedure employing syringe 118. It is contemplated that the first cylinder may include shield 102 or mounting ring 148, and that the second cylinder may include shield 102 or mounting ring 148.

Figure 30:
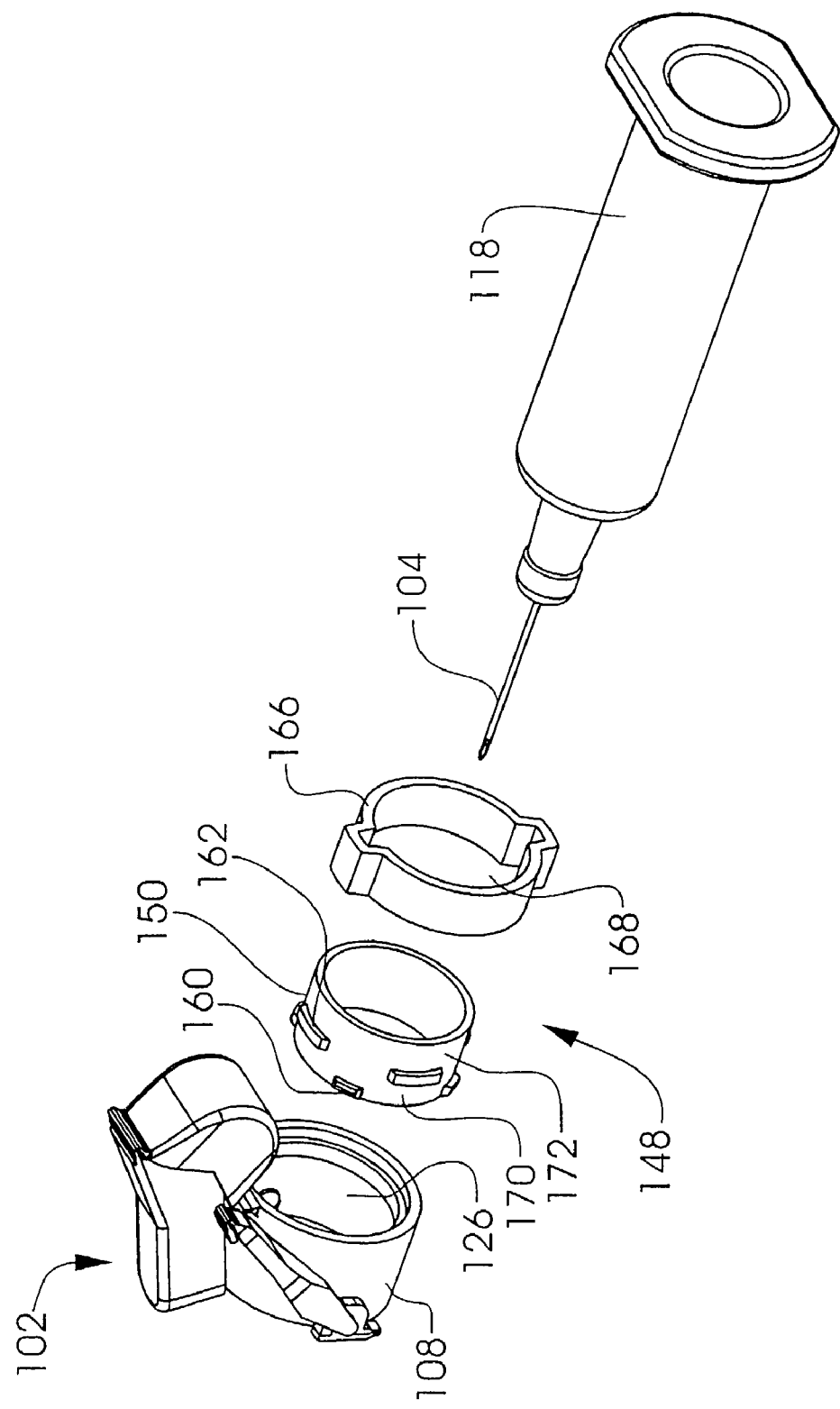
FIG. 30 is an exploded perspective view of an alternate embodiment of the medical needle shield apparatus shown in FIG. 23.
Figure 31:
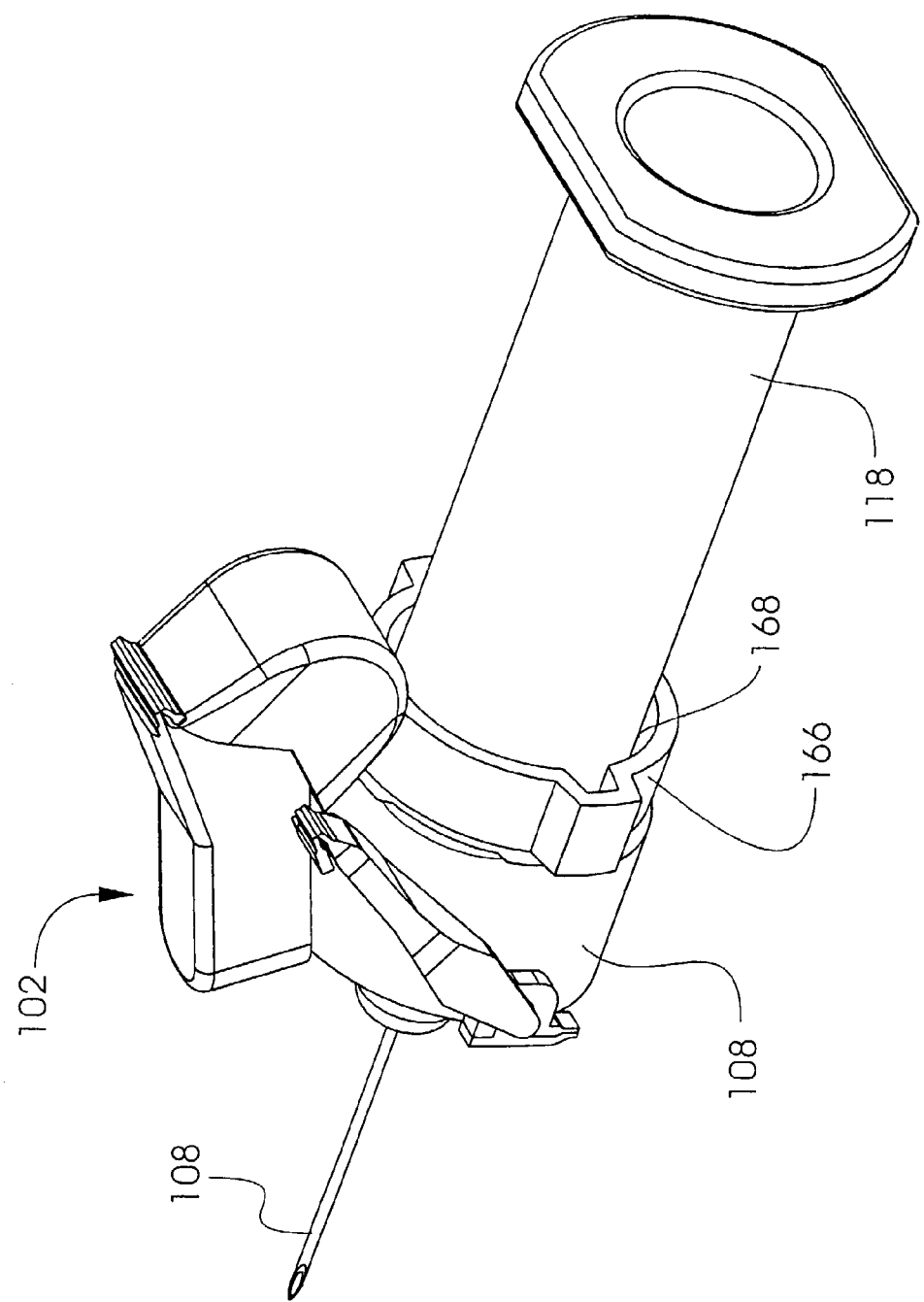
FIG. 31 is a perspective view of the medical needle shield apparatus shown in FIG. 30.

Referring to FIGS. 30 and 31, an alternate embodiment of mounting ring 148 is shown, similar to that described. Outer surface 150 of mounting ring 148 has a collar portion 170 and a clampable portion 172 extending therefrom. Proximal stops 162 and distal stops 160 are formed with outer surface 150. Clampable portion 172 is configured for receiving engagement with a clamp ring 166. Correspondingly, clamp ring 166 defines a clamp cavity 168 for disposal of clampable portion 172 therein. Mounting ring 148 is disposed within collar cavity 126, similar to that described. Clamp ring 166 is configured as a two ear hose clamp. It is contemplated that clamp ring 166 may be alternatively configured as a one ear hose clamp, stepless ear clamp, spring clamp, push retainer, push cap, etc.

Clamp ring 166 is manipulated for orientation with syringe 118. Mounting ring 148 is mounted with syringe 118, similar to that described. Clamp ring 166 is fit over clampable portion 172 of mounting ring 148 such that mounting ring 148 is firmly affixed to syringe 118. It is envisioned that clamp ring 166 may be mounted to an interior surface or to outer surface 150 of mounting ring 148. It is further envisioned that clamp ring 166 may be directly employed with collar 108 of shield 102 and may similarly be mounted to an interior surface or an outer surface of collar 108. Clamp ring 166 and collar 108 may be configured so as to create a press fit in which clamp ring 166 and collar 108 are pressed onto a syringe 118 as a unit.

Figure 32:
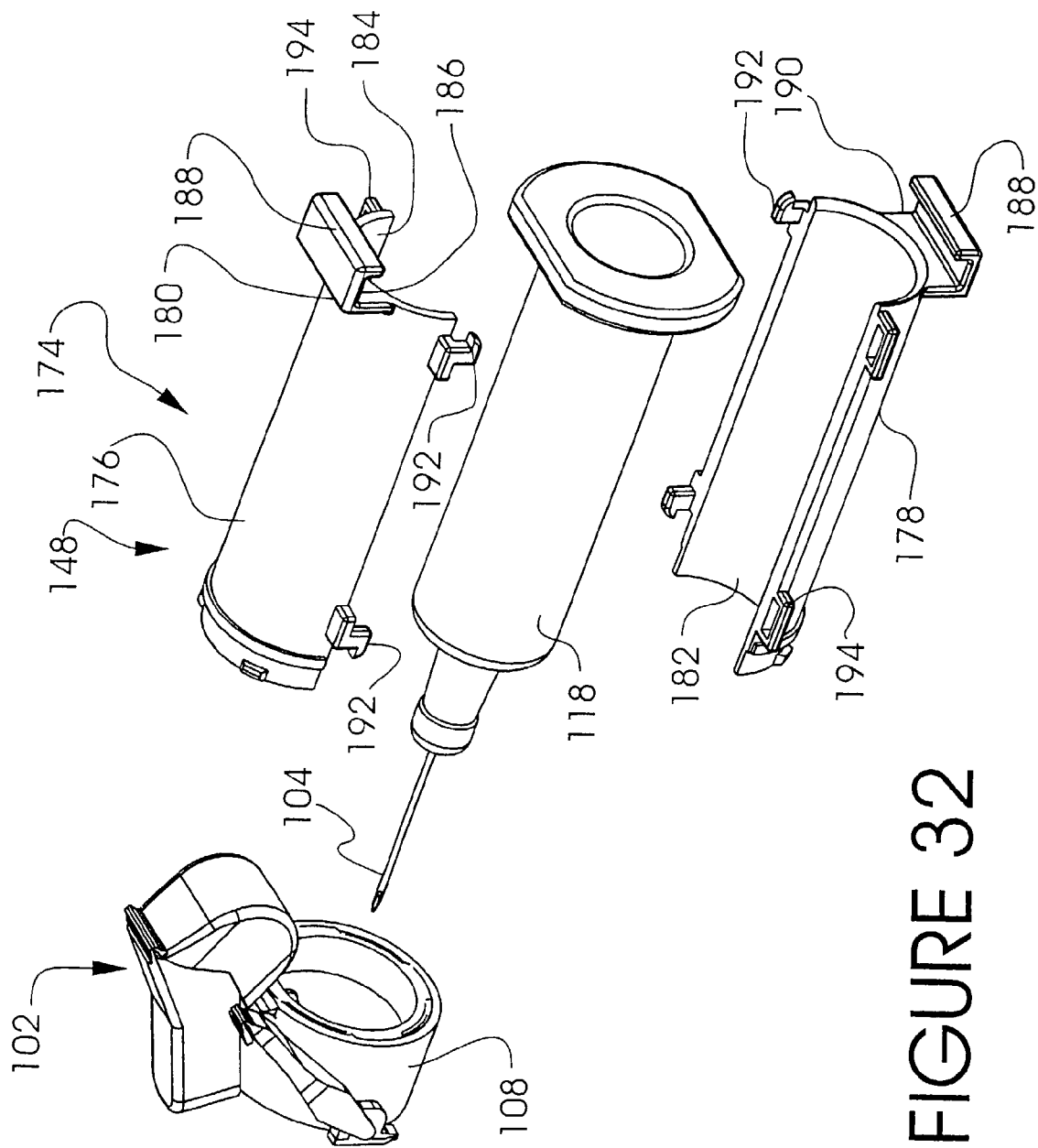
FIG. 32 is an exploded perspective view of another alternate embodiment of the medical needle shield apparatus shown in FIG. 23.
Figure 33:
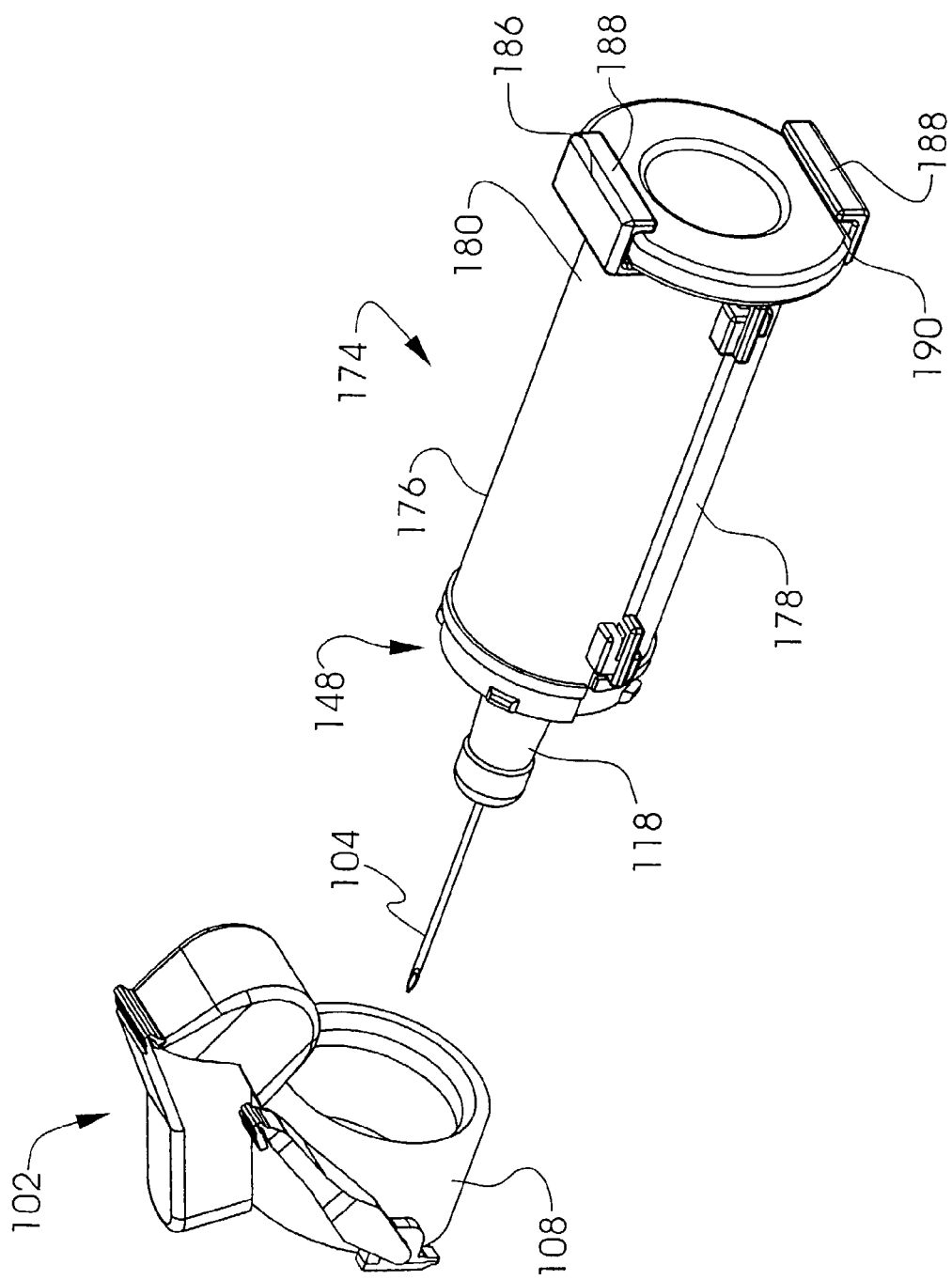
FIG. 33 is a partially exploded perspective view of the medical needle shield apparatus shown in FIG. 32.
Figure 34:
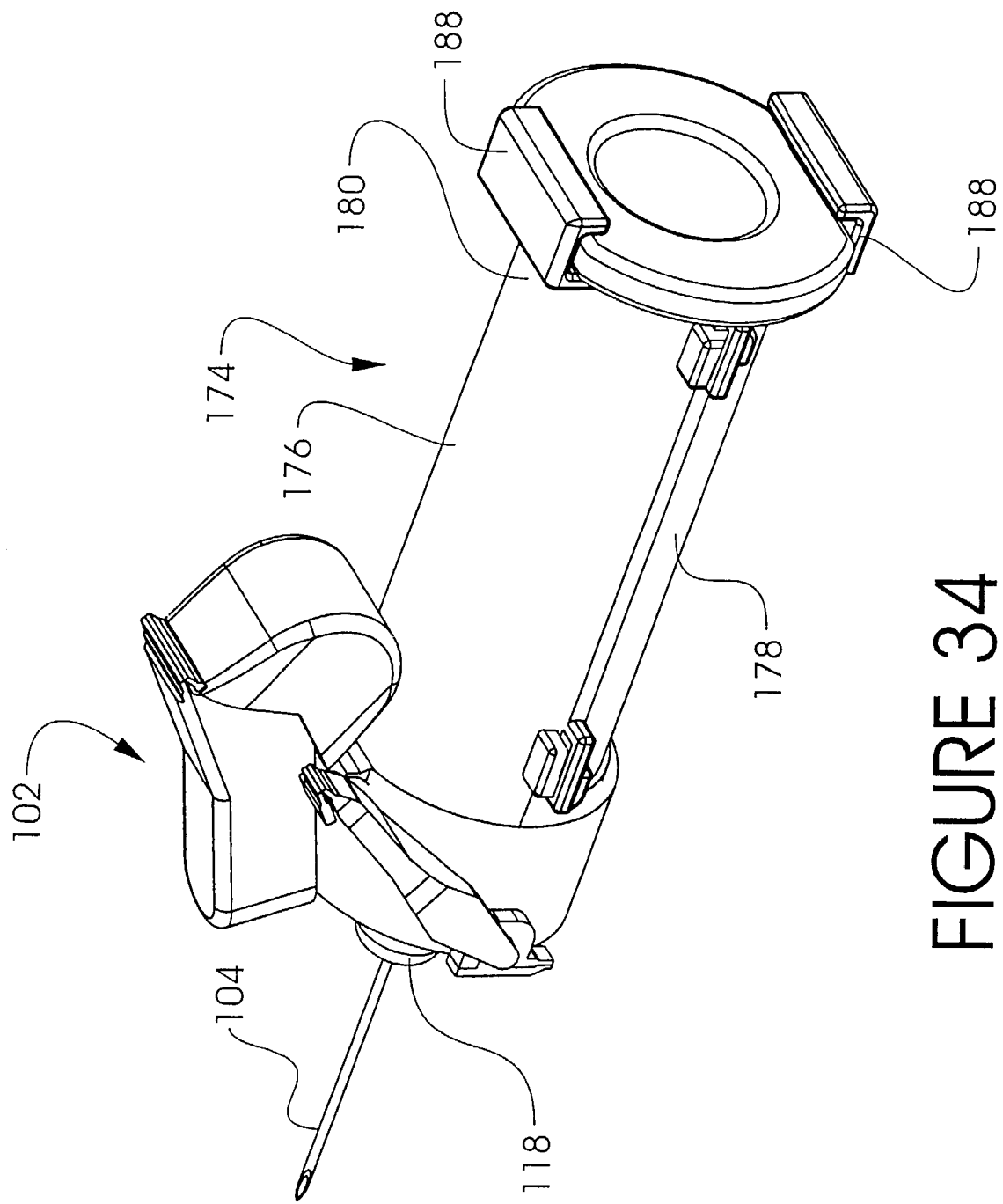
FIG. 34 is a perspective view of the medical needle shield apparatus shown in FIG. 32.

Referring to FIGS. 32–34, another alternate embodiment of mounting ring 148 is shown, similar to those described. Mounting ring 148 includes a cover 174 that has a first cover portion 176 attachable with a second cover portion 178. Cover 174 defines a cover cavity 182 and includes a cover base 180 at a proximal end thereof. Cover 174, and correspondingly cover cavity 182, are configured for support of syringe 118. Mounting ring 148 includes proximal stops 162 and distal stops 160, similar to those described, which cooperate with collar 108 to facilitate mounting of shield 102 with syringe 118, as discussed.

Figure 37:
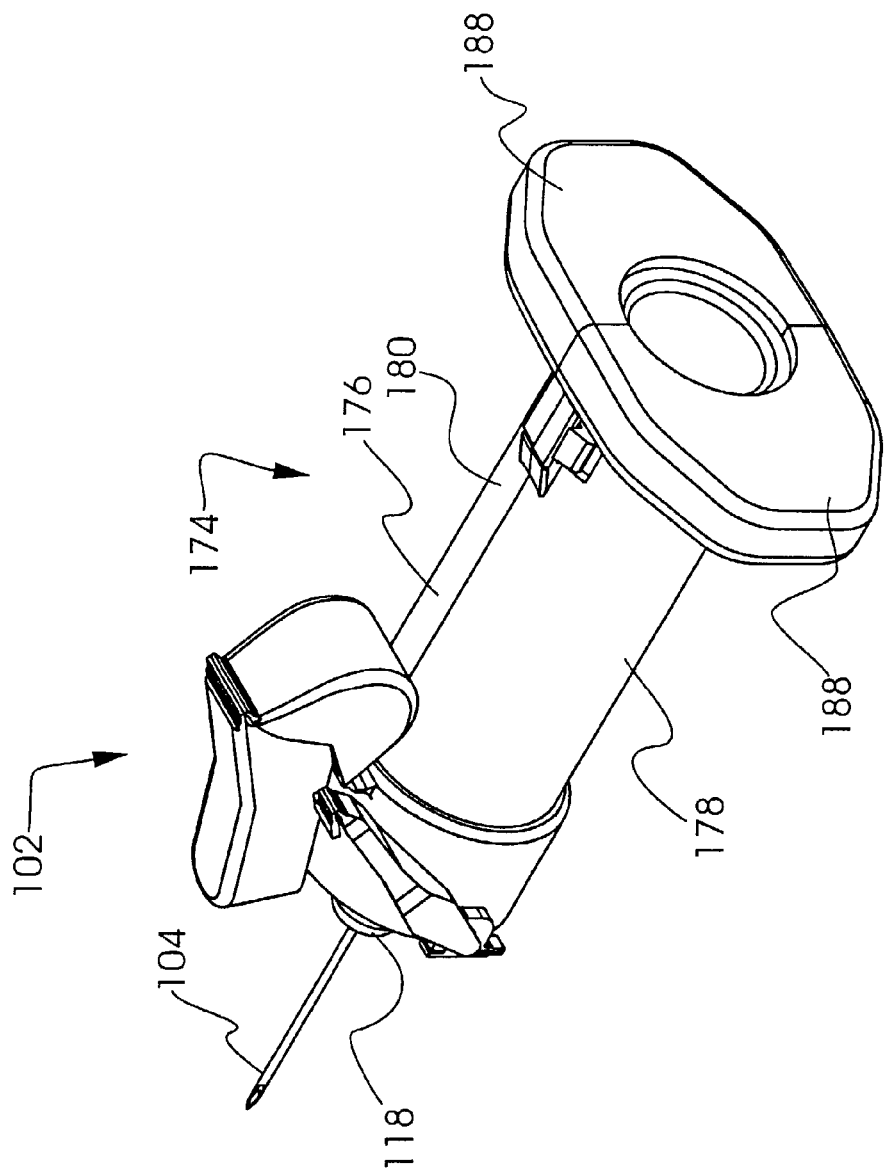
FIG. 37 is a perspective view of an alternate embodiment of the medical needle shield apparatus shown in FIG. 34.

Cover base 180 includes a base opening 184 and a grip channel 186. Grip channel 186 includes grip channel lips 188 that define a grip channel opening 190 configured for receipt of a finger grip of syringe 118. Grip channel lips 188 support the finger grip to facilitate mounting of syringe 118 with mounting ring 148 and prevent rotation of syringe 118 relative to cover 174. It is envisioned that grip channel lips 188 may be configured and dimensioned to support various finger grip configurations. It is envisioned that grip channel lips 188 may be configured and dimensioned to support various finger grip configurations, for example, as show FIG. 37. It is also contemplated that the finger grip configurations may be configured to retain a plunger within the syringe barrel as shown in FIG. 37. It is further envisioned that grip channel 186 may include clips, clamps, etc. to facilitate support of syringe 118.

Figure 35:
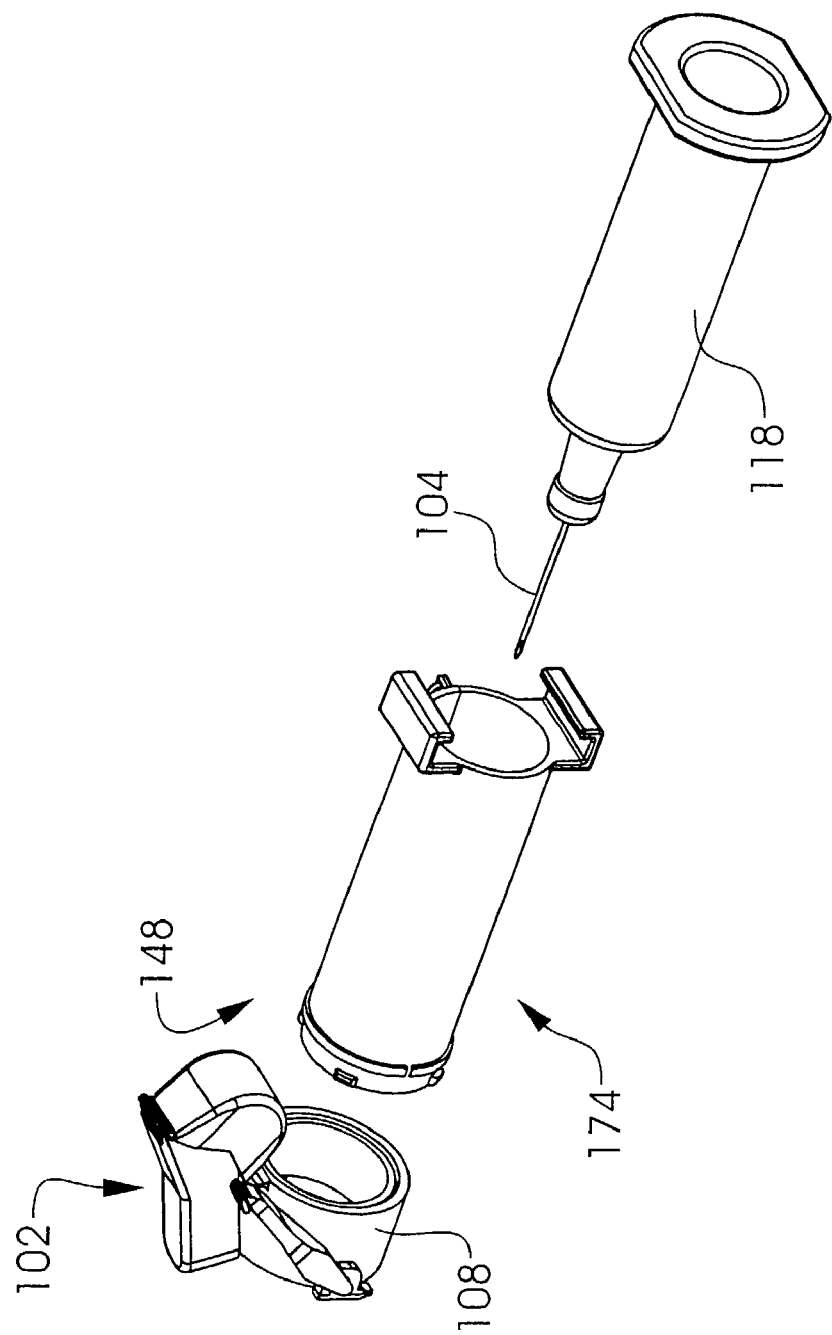
FIG. 35 is an exploded perspective view of an alternate embodiment of the medical needle shield apparatus shown in FIG. 32.
Figure 36:
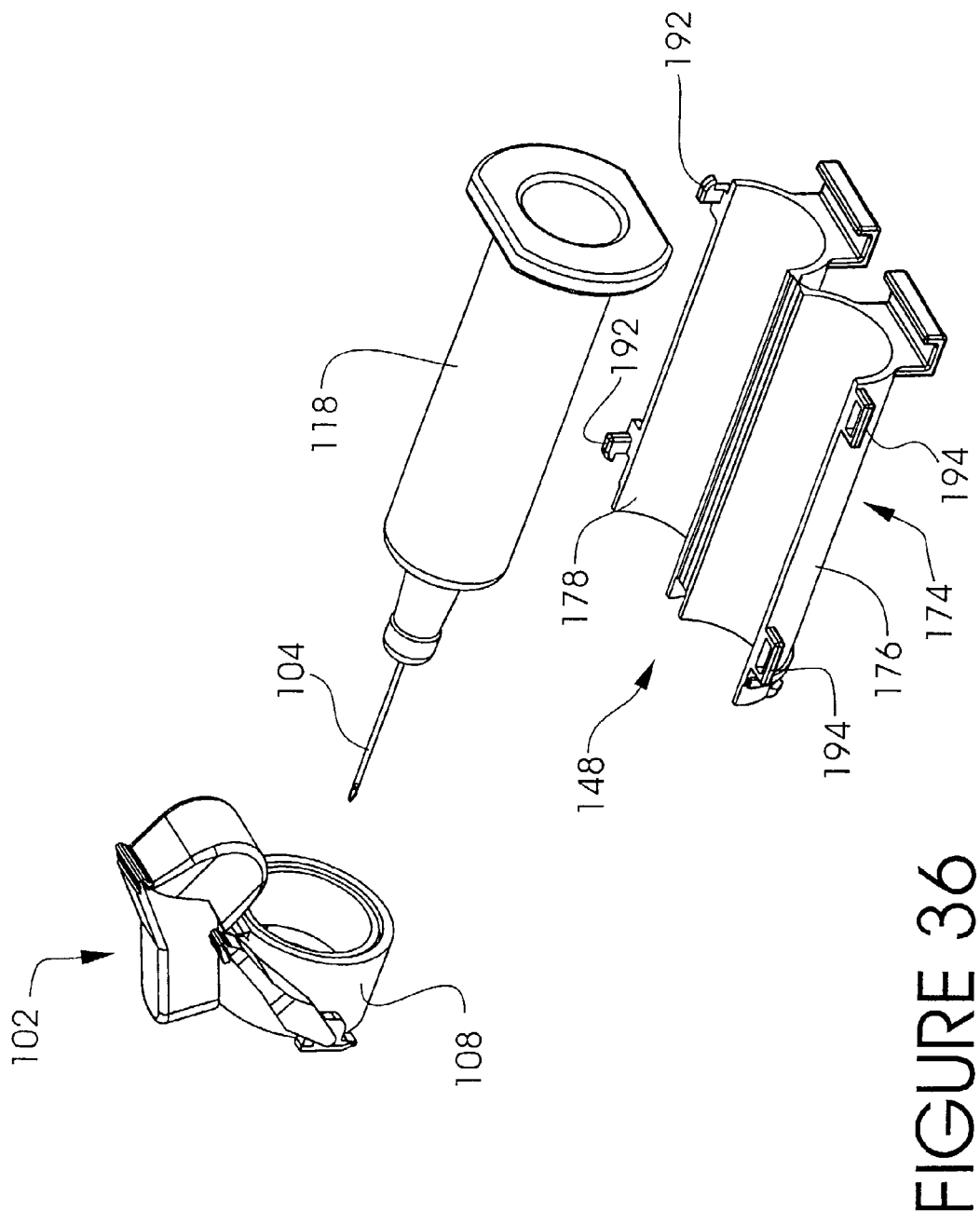
FIG. 36 is an exploded perspective view of another alternate embodiment of the medical needle shield apparatus shown in FIG. 32.

First cover portion 176 and second cover portion 178 are similarly configured and dimensioned for attachment to support syringe 118. Portions 176, 178 are elongated half cylinders that extend from a distal end to a proximal end. It is contemplated that cover 174 may have various cross-sectional configurations, such as, for example, polygonal, elliptical, etc. It is further contemplated that first cover portion 176 may be of a dissimilar configuration and dimension than second cover portion 178. A plurality of cover portions may be used or alternatively, each cover portion may be assembled from a plurality of sections. In an alternate embodiment, as shown in FIG. 35, mounting ring 148 includes a cover 174 having a monolithic tube-type sleeve configuration that slides onto syringe 118 for support thereof. In another alternate embodiment, as shown in FIG. 36, mounting ring 148 includes a cover 174 having a first cover portion 176 and a second cover portion 178 that are hingedly connected along its longitudinal length. This one piece clam-shell type configuration is mounted about syringe 118 for support thereof in a locked engagement that employs male tabs 192 and female slots 194.

First cover portion 176 includes a first portion connection device, such as, for example, male tabs 192 and a second portion connection device, such as, for example, female slots 194, which are alternately disposed on either side and at the proximal and distal ends thereof. Second cover portion 178, reciprocal to first cover portion 176, includes male tabs 192 and female slots 194. Tabs 192 and slots 194 of first cover portion 176 are disposed with corresponding slots 194 and tabs 192 of second cover portion 178, respectively, such that first cover portion 176 can be assembled and locked with second cover portion 178. Upon assembly of first cover portion 176 and second cover portion 178, male tabs 192 engage and latch with female slots 194. It is envisioned that one or a plurality of male tab 192/female slot 194 combinations may be employed. It is further envisioned that the male tab 192/female slot 194 combinations may be variously disposed about cover 174. It is contemplated that the cover portions could be joined through adhesive or welding, e.g., sonic, RF, thermal, etc.

Syringe 118 is disposed within cover cavity 182 such that needle cannula 104 protrudes from the distal end of cover 174 and the finger grip of syringe 118 protrudes from the proximal end cover 174. This configuration advantageously allows syringe 118 and syringe cover 174 to rotate relative to collar 108.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a shield being extensible from a retracted position to an extended position,
   said shield comprising a four-bar linkage comprising a first segment defining a fixed link and being mounted to a medical needle device having a needle extending therefrom,
   said shield further comprising a second segment articulating from said first segment and a third segment defining an input linkage and articulating from said first segment,
   said shield further comprising a fourth segment articulating from said second segment and said third segment, whereby said fourth segment substantially encloses a distal end of said needle.

2. A medical needle shield apparatus as recited in claim 1, wherein said second segment includes an engagement surface for urging said shield from said retracted position such that said second segment and said third segment cooperate to extend said shield to said extended position.

3. A medical needle shield apparatus as recited in claim 1, wherein said third segment includes an engagement surface for urging said shield from said retracted position such that said second segment and said third segment cooperate to extend said shield to said extended position.

4. A medical needle shield apparatus as recited in claim 1, wherein the medical needle shield apparatus is monolithically formed.

5. A medical needle shield apparatus as recited in claim 1, wherein said third segment includes a pair of axially extending arms that articulate from said first segment and are connected to lateral portions of said fourth segment.

6. A medical needle shield apparatus as recited in claim 1, wherein said first segment includes at least one latch and wherein said fourth segment includes at least one catch, said at least one latch being disposed for locking engagement with said at least one catch in said retracted position of the shield.

7. A medical needle shield apparatus as recited in claim 1, wherein said first segment includes at least one catch and wherein said fourth segment includes at least one latch, said at least one catch being disposed for locking engagement with said at least one latch in said extended position of the shield.

8. A medical needle shield apparatus as recited in claim 1, wherein said first segment includes at least one latch and wherein said second segment includes at least one catch, said at least one latch being disposed for locking engagement with said at least one catch in said retracted position of the shield.

9. A medical needle shield apparatus as recited in claim 1, wherein said first segment includes at least one catch and wherein said second segment includes at least one latch, said at least one catch being disposed for locking engagement with said at least one latch in said extended position of the shield.

10. A medical needle shield apparatus as recited in claim 1, wherein said first segment includes at least one latch and wherein said third segment includes at least one catch, said at least one latch being disposed for locking engagement with said at least one catch in said retracted position of the shield.

11. A medical needle shield apparatus as recited in claim 1, wherein said first segment includes at least one catch and wherein said third segment includes at least one latch, said at least one catch being disposed for locking engagement with said at least one latch in said extended position of the shield.

12. A medical needle shield apparatus as recited in claim 1, wherein said fourth segment includes a lock that engages said needle in said extended position of the shield.

13. A medical needle shield apparatus as recited in claim 1, wherein the fourth segment includes a nose portion defining a cavity for disposal of said needle in said extended position of the shield.

14. A medical needle shield apparatus as recited in claim 1, wherein said second segment includes a lock that engages said needle in said extended position of the shield.

15. A medical needle shield apparatus as recited in claim 1, wherein said third segment includes a lock that engages said needle in said extended position of the shield.

16. A medical needle shield apparatus as recited in claim 1, wherein said third segment is configured to facilitate extension of said shield without support of said needle.

17. A medical needle shield apparatus as recited in claim 1, wherein the medical needle shield apparatus is monolithically formed with the medical needle device.

18. A medical needle shield apparatus comprising:
a shield including a plurality of articulating segments that facilitate extension of the shield from a retracted position to an extended position, the plurality of segments including a first segment defining a collar, said collar having an inner surface that defines a cavity, said inner surface including at least one first interlock; and
a mounting ring configured for mounting to a medical needle device, said mounting ring having an outer surface that includes at least one second interlock, said collar being configured for relative rotational movement with said mounting ring such that the outer surface of said mounting ring is disposed within said cavity of said collar, said at least one first interlock being disposed adjacent the outer surface of the mounting ring such that the at least one second interlock prevents movement of the collar in the proximal and axial direction relative to a longitudinal axis of the medical needle device.

19. A medical needle shield apparatus as recited in claim 18, wherein said first interlock includes at least one radially inward projecting collar stop.

20. A medical needle shield apparatus as recited in claim 18, wherein said second interlock includes at least one radially outward projecting proximal stop and at least one radially projecting distal stop, such that the at least one proximal stop prevents distal axial movement, relative to a longitudinal axis of the medical needle device, of the collar and the at least one distal stop prevents proximal axial movement of the collar.

21. A medical needle shield apparatus as recited in claim 18, wherein said plurality of segments includes a second segment articulating from the first segment and a third segment articulating from said first segment, the plurality of segments further including a fourth segment articulating from said second segment and said third segment.

22. A medical needle shield apparatus as recited in claim 21, wherein said second segment includes an engagement surface for urging said shield from the retracted position to the extended position.

23. A medical needle shield apparatus as recited in claim 21, wherein said third segment includes an engagement surface for urging said shield from the retracted position to the extended position.

24. A medical needle shield apparatus as recited in claim 21, wherein said fourth segment is configured to enclose a distal end of a needle of said medical needle drive, said fourth segment including a lock that engages to said needle when said shield is in said extended position.

25. A medical needle shield apparatus as recited in claim 18, wherein said mounting ring includes a clamp ring mounted about said outer surface of said mounting ring in a fit engagement.

26. A medical needle shield apparatus as recited in claim 18, wherein said mounting ring is mounted to the medical needle device via an adhesive.

27. A medical needle shield apparatus as recited in claim 18, wherein said mounting ring includes a cover having a first cover portion attached with a second cover portion, said cover defining a cover cavity that supports said medical needle device.

28. A medical needle shield apparatus as recited in claim 27, wherein said cover includes a grip channel mounted with said cover for disposal adjacent a proximal end of the medical needle device, the grip channel defining a cavity for receiving a portion of the medical needle device.

29. A medical needle shield apparatus as recited in claim 28, wherein said medical needle device includes a syringe having a plunger mounted therewith, said cavity of said grip channel supporting said plunger adjacent a proximal end of said syringe.

30. A medical needle shield apparatus as recited in claim 27, wherein said first cover portion is hingedly connected with said second cover portion.

31. A medical needle shield apparatus as recited in claim 27, wherein said first cover portion is engageable with said second cover portion for lockable engagement therewith.

32. A medical needle shield apparatus as recited in claim 18, wherein the medical needle shield apparatus is monolithically formed with the medical needle device.

33. A medical needle shield apparatus comprising:
a shield extensible from a retracted position to an extended position, said shield including a cyndrical collar, a proximal segment articulating from said collar and an input link articulating from said collar, a distal segment articulating from said proximal segment and said input link, wherein said proximal segment includes a pair of axially extending arms that articulate from said collar and are connected to lateral portions of said distal segment,
said collar defining an inner surface that defines a cavity, said inner surface including a plurality of radially inward projecting collar stops and said input link including an engagement surface that is engageable to urge said shield from said retracted position such that said input link and said proximal segment cooperate to extend said shield to said extended position, whereby said distal segment includes a nose portion that substantially encloses a distal end of a needle extending from a syringe; and
a mounting ring configured for mounting to said syringe, said mounting ring having an outer surface that includes a plurality of radially outward projecting proximal stops and a plurality radially projecting distal stops, said collar being configured for relative rotational movement with said mounting ring such that said mounting ring is disposed in an interlocking orientation with said collar whereby said plurality of collar stops are disposed adjacent the outer surface of the mounting ring such that the plurality of proximal stops prevent distal axial movement, relative to a longitudinal axis of the syringe, of the collar and the pluyality of distal stops prevent proximal axial movement of the collar.

* * * * *